(12) United States Patent
Toji

(10) Patent No.: US 10,485,515 B2
(45) Date of Patent: Nov. 26, 2019

(54) ULTRASOUND DIAGNOSTIC DEVICE AND METHOD FOR CONTROLLING ULTRASOUND DIAGNOSTIC DEVICE

(71) Applicant: KONICA MINOLTA, INC., Chiyoda-ku, Tokyo (JP)

(72) Inventor: Bumpei Toji, Hashima (JP)

(73) Assignee: KONICA MINOLTA, INC., Tokyo (JP)

(*) Notice: Subject to any disclaimer, the term of this patent is extended or adjusted under 35 U.S.C. 154(b) by 1002 days.

(21) Appl. No.: 14/983,239

(22) Filed: Dec. 29, 2015

(65) Prior Publication Data
US 2016/0213352 A1 Jul. 28, 2016

(30) Foreign Application Priority Data
Jan. 28, 2015 (JP) .................................. 2015-014367

(51) Int. Cl.
A61B 8/08 (2006.01)
A61B 8/00 (2006.01)

(52) U.S. Cl.
CPC ............ *A61B 8/485* (2013.01); *A61B 8/5207* (2013.01); *A61B 8/5223* (2013.01); *A61B 8/469* (2013.01)

(58) Field of Classification Search
CPC ..... A61B 8/485; A61B 8/5207; A61B 8/5223; A61B 8/469
See application file for complete search history.

(56) References Cited

U.S. PATENT DOCUMENTS

| 9,895,137 B2 | 2/2018 | Tabaru et al. |
| 2011/0066030 A1* | 3/2011 | Yao ........................ A61B 8/485 600/438 |
| 2012/0123263 A1 | 5/2012 | Osaka et al. |
| 2013/0218011 A1 | 8/2013 | Benson et al. |

(Continued)

FOREIGN PATENT DOCUMENTS

| JP | 2014000260 A | 1/2014 |
| WO | 2011004661 A1 | 1/2011 |
| WO | 2014136502 A1 | 9/2014 |

OTHER PUBLICATIONS

Japanese Office Action (and English language translation thereof) dated Apr. 24, 2018 issued in Japanese Application No. 2015-014367.

*Primary Examiner* — Peter Luong
(74) *Attorney, Agent, or Firm* — Holtz, Holtz & Volek PC

(57) ABSTRACT

An ultrasound diagnostic device that transmits a push pulse into a subject and detects a shear wave propagating to adjacent tissue by repeating transmission of ultrasound to the subject and reception of reflected ultrasound from the subject, including a displacement detector that obtains reception signals in a time series by transmitting ultrasound to the subject and receiving reflected ultrasound from the subject, subsequent to transmission of the push pulse, and detects a displacement amount of the tissue inside the subject at each point in time at which the reception signals are respectively obtained; a wavefront extractor that extracts, based on the displacement amount of the tissue at each of the points in time, a wavefront of the shear wave at the corresponding point in time; and a wavefront image processor that generates a wavefront image that indicates a wavefront of the shear wave at each of the points in time.

16 Claims, 17 Drawing Sheets

(56) References Cited

U.S. PATENT DOCUMENTS

2015/0133782 A1\* 5/2015 Yoshikawa ............ A61B 8/485
  600/438
2015/0173718 A1  6/2015 Tabaru et al.

\* cited by examiner

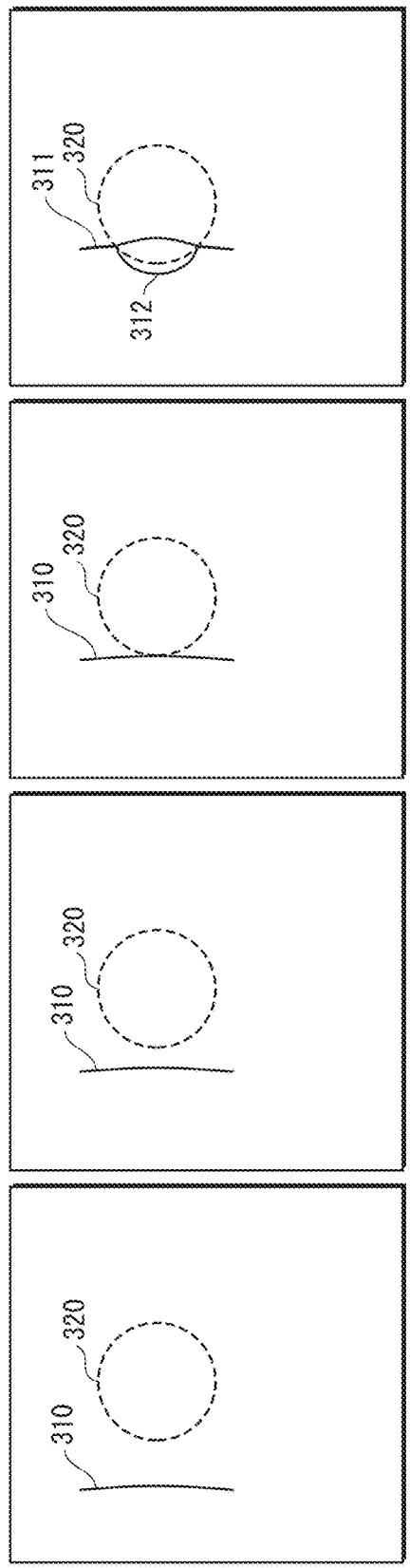

ULTRASOUND DIAGNOSTIC DEVICE AND METHOD FOR CONTROLLING ULTRASOUND DIAGNOSTIC DEVICE

This application is on an application No. 2015-014367 filed in Japan on Jan. 28, 2015, the contents of which are hereby incorporated by reference.

BACKGROUND OF THE INVENTION

(1) Field of the Invention

The present invention relates to imaging processing performed by an ultrasound diagnostic device, and in particular to hardness measurement using a shear wave.

(2) Description of the Related Art

Recent years have seen the widespread use of ultrasound diagnostic devices that have the function of evaluating the hardness of a tissue inside the subject. There are roughly two methods for evaluating the hardness using an ultrasound diagnostic device. One method is to apply pressure to a tissue inside the subject from the body surface by using an ultrasound probe, release the pressure, and then evaluate the relative hardness of the tissue inside the subject based on the magnitude of distortion of the tissue inside the subject relative to the pressure. With this method, it is possible to evaluate a relative hardness inside the subject, which indicates whether the tissue is hard or soft compared to surrounding tissues.

The other method is to cause a region of interest (ROI) inside the subject to generate a shear wave, and measure the propagation speed of the shear wave by obtaining the displacement of the tissue within the region of interest in a time series. Since the propagation speed of the shear wave changes depending on the elastic modulus of the tissue, this method makes it possible to evaluate the absolute hardness of the tissue. As a technique to generate the shear wave, a technique called acoustic radiation force impulse (ARFI) can be used for example, by which the tissue inside the subject is displaced by the sound pressure of ultrasound.

With this method, however, there are cases where the speed of the shear wave cannot be properly calculated. One example is the case where the displacement of the tissue within the region of interest is irregular. In such a case, a displacement due to a movement of the entire tissue cannot be accurately extracted, and accordingly, the displacement due to the movement of the entire tissue is mixed in with a displacement due to the shear wave, and the accuracy in calculating the speed of the shear wave decreases. Another example is the case where the shear wave undergoes deflection or reflection at the boundary of the tissue. Conventionally, the speed of a shear wave is calculated on the assumption that, for each of several points within a tissue, the time at which the displacement reaches its maximum for the first time is the arrival time of the first wavefront of the shear wave arriving at the corresponding point. That is, the method is predicated on the case where a shear wave travels away from its source, and therefore, in other cases, the speed of the shear wave cannot be calculated, or the calculation results are inaccurate.

In order to address such a problem, when the arrival time of a shear wave at a given point within the tissue is significantly different from the arrival times at its surrounding points, or when the speed of the shear wave cannot be calculated, it is conventionally proposed to refrain from calculating the speed of the shear wave at the given point or inform the examiner that the speed of the shear wave at the given point has low reliability. Also, according to the technique disclosed in Japanese Patent Application Publication No. 2014-260, the arrival time distribution of the shear wave is shown on a shear wave arrival image, in which hues are allocated according to the arrival time of the shear wave, and thus the speed of the shear wave is visually shown, and also regions where the reliability of the speed of the shear wave is low are explicitly shown.

SUMMARY OF THE INVENTION

Problems to be Solved by the Invention

However, according to the conventional technique by which the examiner is informed of the reliability of the speed of the shear wave, it is impossible for the examiner to know the specific reason why the speed of the shear wave could not be obtained. According to the technique disclosed in Japanese Patent Application Publication No. 2014-260, the shear wave arrival image is generated based on the presumption that the shear wave travels away from its source, and distorted regions in the image such as regions with a patchy pattern are considered as regions in which the reliability of the speed of the shear wave is low. Therefore, for example, when the low reliability of the speed of the shear wave results from reflection or the like of the shear wave, it is impossible to know the specific location where the reflection or the like occurred or the influence of the reflection or the like on the results of measurement of the speed of the shear wave. Therefore, with the conventional technique, the examiner needs to blindly conduct re-measurement of the speed of the shear wave, with no idea of how to obtain the speed of the shear wave.

The present disclosure is made in view of the problems above, and aims to provide the examiner with information that is necessary for enabling the shear wave to properly propagate, and to thereby improve the ease of use for the examiner.

Means for Solving the Problems

An ultrasound diagnostic device pertaining to one aspect of the present disclosure is an ultrasound diagnostic device that transmits a push pulse, which is ultrasound that converges on a particular part inside a subject to apply physical pressure to tissue at the particular part, by using an ultrasound probe, and detects a process in which the tissue at the particular part acts as a vibration source due to the pressure and a shear wave propagates to adjacent tissue, by repeating transmission of ultrasound to the subject and reception of reflected ultrasound from the subject subsequent to transmission of the push pulse, the ultrasound diagnostic device comprising an ultrasound signal processing circuit, wherein the ultrasound signal processing circuit includes: a displacement detector that obtains a plurality of reception signals in a time series by performing transmission of ultrasound to the subject and reception of reflected ultrasound from the subject, subsequent to transmission of the push pulse, and detects a displacement amount of the tissue inside the subject at each of a plurality of points in time at which the plurality of reception signals are respectively obtained; a wavefront extractor that extracts, based on the displacement amount of the tissue at each of the plurality of points in time at which the plurality of reception signals are respectively obtained, a wavefront of the shear wave at the corresponding point in time; and a wavefront image processor that generates a wavefront image that indicates a wavefront of the shear wave at each of the plurality of points in time at which the plurality of reception signals are respectively obtained.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIGS. 8A to 8H are diagrams showing the propagation of wavefronts according to Embodiment 1 in a time series;

DESCRIPTION OF EMBODIMENTS

The following is a description of embodiments of the present invention with reference to the drawings.

Embodiment 1

Figure 1:
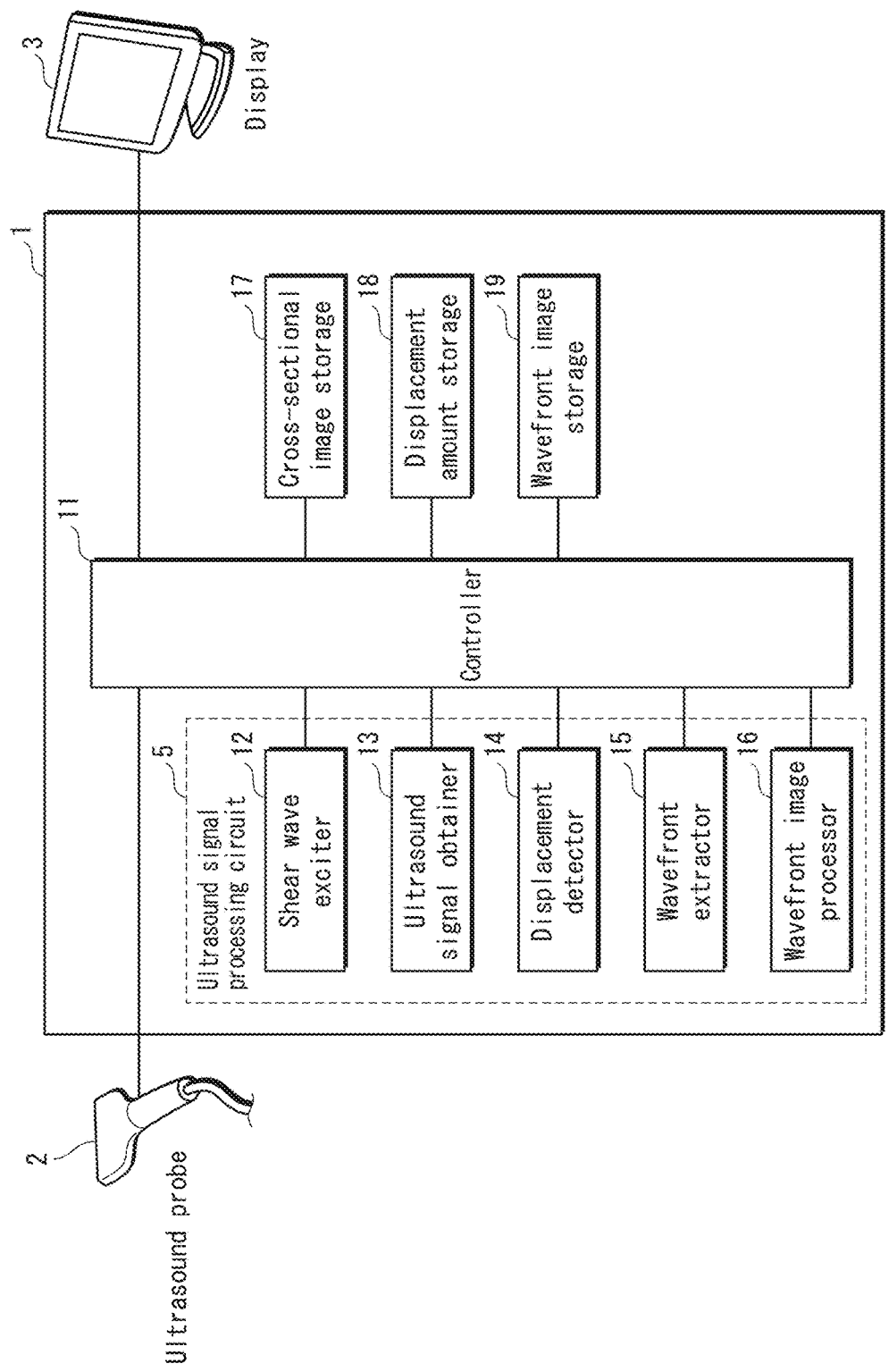
FIG. 1 is a block diagram of an ultrasound diagnostic device 1 according to Embodiment 1.

FIG. 1 shows a block diagram of an ultrasound diagnostic device 1 according to Embodiment 1. The ultrasound diagnostic device 1 includes a controller 11, a shear wave exciter 12, an ultrasound signal obtainer 13, a displacement detector 14, a wavefront extractor 15, a wavefront image processor 16, a cross-sectional image storage 17, a displacement amount storage 18, and a wavefront image storage 19. The shear wave exciter 12, the ultrasound signal obtainer 13, the displacement detector 14, the wavefront extractor 15, and the wavefront image processor 16 constitute an ultrasound signal processing circuit 5. Also, the controller 11 is configured such that an ultrasound probe 2 and a display 3 are each connectable thereto. FIG. 1 shows a situation where the ultrasound probe 2 and the display 3 have been connected to the ultrasound diagnostic device 1.

The ultrasound probe 2 has, for example, a plurality of transducers (not shown in the drawings) arranged in a one-dimensional array. Each transducer includes, for example, lead zirconate titanate (PZT). The ultrasound probe 2 receives electrical signals generated by the shear wave exciter 12 (hereinafter referred to as "the ARFI drive signals") or electrical signals generated by the ultrasound signal obtainer 13 (hereinafter referred to as "the transmission drive signals") from the controller 11, and converts the received signals into ultrasound waves. The ultrasound probe 2 transmits, to the measurement target inside the subject, an ultrasound beam composed of a plurality of ultrasound waves, which have been converted from the ARFI drive signals or the transmission drive signals and which are emitted from the plurality of transducers, with the transducer side external surface of the ultrasound probe 2 being in contact with a surface such as a skin surface of the subject. Then, the ultrasound probe 2 receives, from the measurement target, a plurality of reflected ultrasound waves, which correspond to the transmission ultrasound waves based on the transmission drive signals, converts the reflected ultrasound waves to electrical signals respectively (hereinafter referred to as "the element reception signals") by using the plurality of transducers, and supplies the element reception signals to the ultrasound signal obtainer 13 via the controller 11. Note that although the shear wave exciter 12 and the ultrasound signal obtainer 13 described here are assumed to have different configurations, the ARFI drive signals may be generated by a component having a configuration that is the same as the configuration for generating the transmission drive signals of the ultrasound signal obtainer 13.

The shear wave exciter 12 generates the ARFI drive signals, which are electrical signals used for causing the ultrasound probe 2 to emit a push pulse. A push pulse is pulsed ultrasound used for displacing a tissue inside the subject in order to generate a shear wave inside the subject. Specifically, a push pulse is ultrasound that is focused on a given single point within the region of interest inside the subject and that has a wavenumber that is greater than the wavenumber of transmission ultrasound waves, which are described below. Therefore, the ARFI drive signals are pulsed electrical signals that are generated such that the ultrasound waves respectively emitted from the transducers constituting the ultrasound probe 2 reach the focal point.

The ultrasound signal obtainer 13 generates the transmission drive signals, which are electrical signals used for causing the ultrasound probe 2 to emit transmission ultrasound waves. The transmission drive signals are pulsed electrical signals which differ in timing for the respective transducers, and are generated such that the transmission ultrasound waves respectively emitted from the transducers that constitute the ultrasound probe 2 reach the transmission focal point at the same time. The ultrasound signal obtainer 13 performs a delay-and-sum process on the element reception signals that are based on the reflected ultrasound waves, thereby generating acoustic line signals. The ultrasound signal obtainer 13 outputs the generated acoustic line signals to the cross-sectional image storage 17 via the controller 11.

The displacement detector 14 obtains, from the cross-sectional image storage 17 via the controller 11, a plurality of acoustic line signals (hereinafter referred to as "cross-sectional image signals") related to one cross-sectional image that is to be subjected to displacement detection, and a plurality of acoustic line signals (hereinafter referred to as "reference cross-sectional image signals") related to one cross-sectional image that serves as a reference image. The reference cross-sectional image signals are used for extracting a displacement due to the shear wave from the cross-sectional image signals, and specifically, the reference cross-sectional image signals are cross-sectional image signals obtained by capturing an image of the region of interest before a push pulse is emitted. The displacement detector 14 then detects, from differences between the cross-sectional image signals and the reference cross-sectional image signals, the respective displacements of the pixels in the cross-sectional image signals, and generates a displacement image by associating the displacements with the coordinates of the pixels. The displacement detector 14 outputs the generated displacement image to the displacement amount storage 18 via the controller 11.

Figure 2:
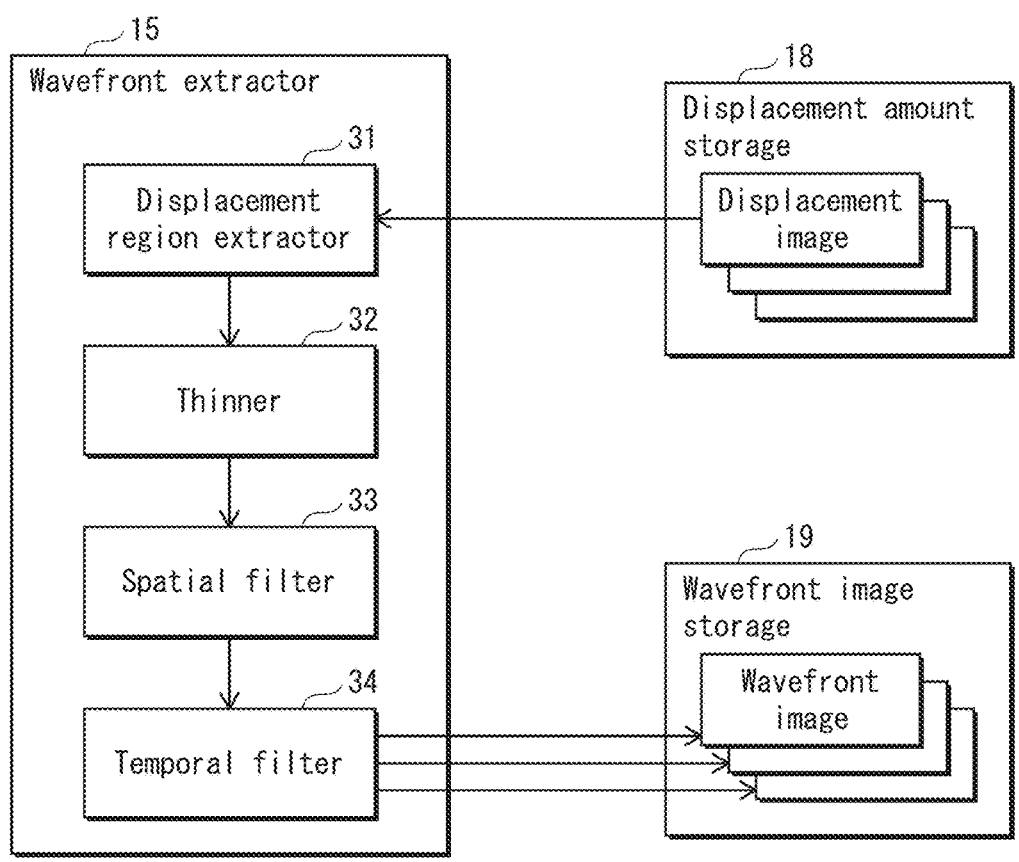
FIG. 2 is a functional block diagram of a wavefront extractor 15 according to Embodiment 1.

The wavefront extractor 15 obtains the displacement image from the displacement amount storage 18 via the controller 11. The wavefront extractor 15 extracts wavefronts of the shear wave from a displacement image, and generates one piece of wavefront image data for the wavefronts of one displacement image. FIG. 2 shows a functional block diagram of the wavefront extractor 15. The wavefront extractor 15 includes a displacement region extractor 31, a thinner 32, a spatial filter 33, and a temporal filter 34.

The displacement region extractor 31 extracts, from the displacement image, a displacement region with a large displacement. The thinner 32 extracts the wavefronts by performing a thinning process on the displacement region, thereby generating a piece of wavefront image data. The spatial filter 33 removes wavefronts that have been erroneously detected from the wavefront image, by using the shape of the wavefronts. The temporal filter 34 detects the temporal transition of the wavefronts from a plurality of wavefront images, and removes wavefronts that have been erroneously detected. Further details are described later. The wavefront extractor 15 outputs the generated wavefront image data to the wavefront image storage 19 via the controller 11.

The wavefront image processor 16 obtains the wavefront image data from the wavefront image storage 19 via the controller 11. The wavefront image processor 16 modifies the mode of displaying each wavefront such that wavefronts at the same point in time are displayed in the same mode. The wavefront image processor 16 outputs the wavefront image data that has undergone modification.

The cross-sectional image storage 17, the displacement amount storage 18, and the wavefront image storage 19 respectively store cross-sectional images, displacement images, and wavefront image data. The cross-sectional image storage 17, the displacement amount storage 18, and the wavefront image storage 19 are each realized with a storage medium such as a RAM, a flash memory, or a hard disk.

In addition to controlling each component described above, the controller 11 is also capable of outputting, to the display 3, a plurality of wavefront images, which have been modified by the wavefront image processor 16, in the form of a moving image.

The display 3 displays images and moving images output by the controller 11. The display 3 is realized with a display device such as a liquid crystal display or an organic EL display.

The controller 11, the shear wave exciter 12, the ultrasound signal obtainer 13, the displacement detector 14, the wavefront extractor 15, and the wavefront image processor 16 are each realized with hardware such as a field programmable gate array (FPGA) or an application specific integrated circuit (ASIC). Alternatively, the controller 11, the shear wave exciter 12, the ultrasound signal obtainer 13, the displacement detector 14, the wavefront extractor 15, and the wavefront image processor 16 may be realized with a combination of a memory, programmable devices such as a central processor (CPU) and a graphic processor (GPU), and software, such that each of the units is individually realized with the combination, or the units are divided into groups composed of two or more units and each group is realized with the combination.

Operations

Figure 3:
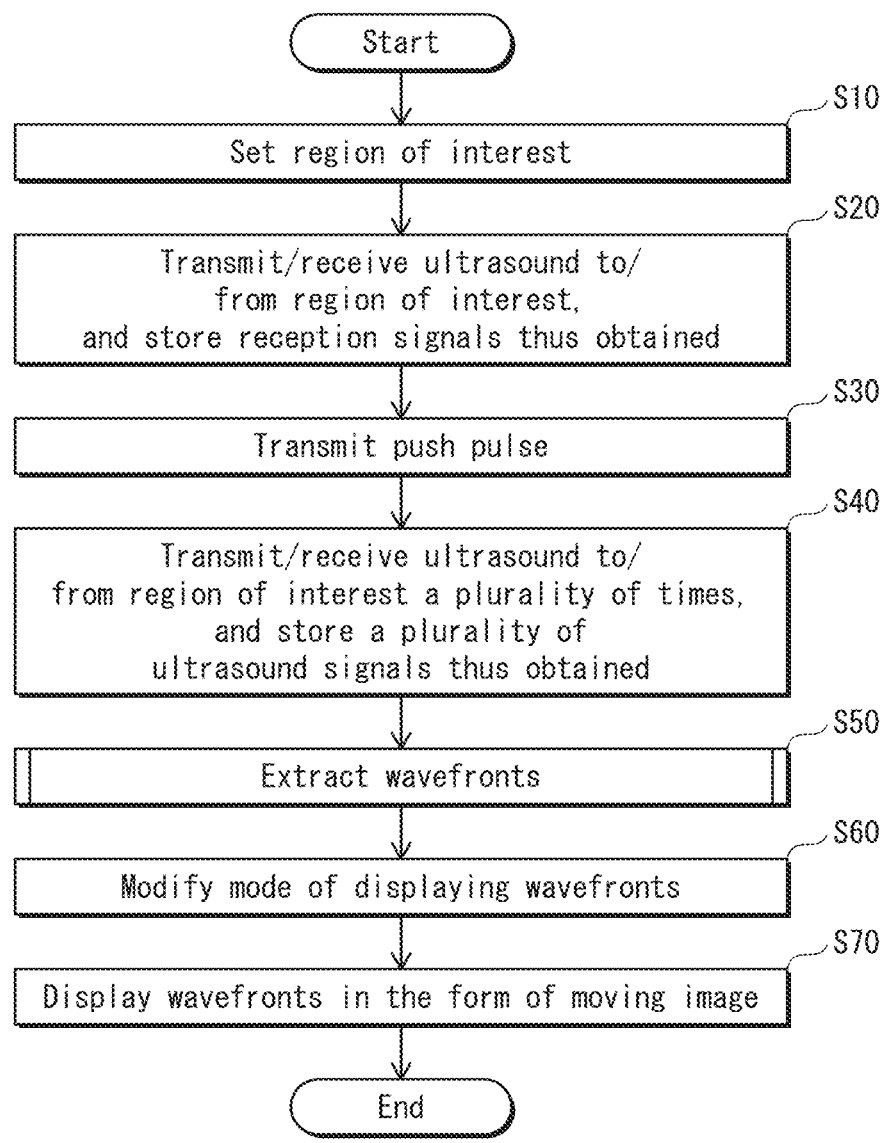
FIG. 3 is a flowchart showing overall operations of the ultrasound diagnostic device 1 according to Embodiment 1.

The following describes the operations of the ultrasound diagnostic device 1 according to Embodiment 1. FIG. 3 is a flowchart showing overall operations of the ultrasound diagnostic device 1.

First, the controller 11 sets the region of interest inside the subject (step S10). The region of interest is set by, for example, displaying the newest cross-sectional image recorded in the cross-sectional image storage 17 on the display 3, and prompting the examiner to specify the region of interest via the use of an input unit (not shown in the drawings) such as a touch panel, a mouse, or a track ball. Note that the method for setting the region of interest is not limited to the above, and, for example, the entire region of the cross-sectional image may be considered as the region of interest, or a certain range including a central portion of the cross-sectional image may be considered as the region of interest.

Next, ultrasound is transmitted to and received from the region of interest, and reception signals thus obtained are stored (step S20). Specifically, the following operations are performed. First, a transmission event is performed as follows. First, the ultrasound signal obtainer 13 generates a pulsed transmission signal. Next, the ultrasound signal obtainer 13 performs, on the transmission signal, transmission beamforming, by which a delay time with respect to each transducer of the ultrasound probe 2 is set, and generates a plurality of transmission drive signals respectively corresponding to the transducers of the ultrasound probe 2. Each transducer of the ultrasound probe 2 converts the corresponding transmission drive signal into an ultrasound wave, and thus an ultrasound beam is emitted to the inside of the subject. Next, each transducer of the ultrasound probe 2 obtains a reflected ultrasound wave reflected from the inside of the subject, and converts the reflected ultrasound wave into an element reception signal. The ultrasound signal obtainer 13 performs a delay-and-sum process on the element reception signals, thereby generating an acoustic line signal. The controller 11 obtains one acoustic line signal for each transmission event from the ultrasound signal obtainer 13, and stores a plurality of acoustic line signals that constitute one cross-sectional image to the cross-sectional image storage 17 as cross-sectional image signals.

Next, a push pulse is transmitted (step S30). Specifically, the shear wave exciter 12 generates a pulsed ARFI signal. Next, the shear wave exciter 12 performs transmission beamforming on the ARFI signal, by which a delay time with respect to each transducer of the ultrasound probe 2 is set, and generates a plurality of ARFI drive signals respectively corresponding to the transducers of the ultrasound probe 2. Each transducer of the ultrasound probe 2 converts the corresponding ARFI drive signal into an ultrasound wave, and thus a push pulse is emitted to the inside of the subject.

Figure 4A:
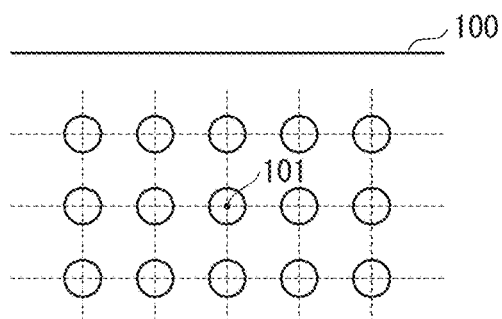
FIGS. 4A to 4E are schematic diagrams showing the generation and propagation of a shear wave in a time series.
Figure 4B:
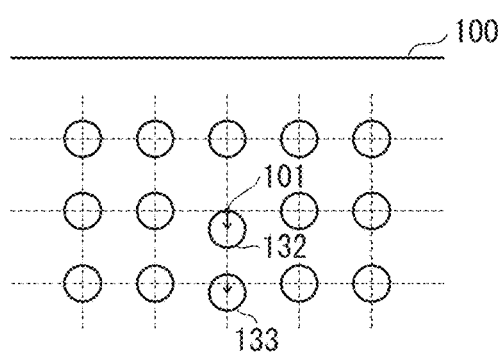
Figure 4C:
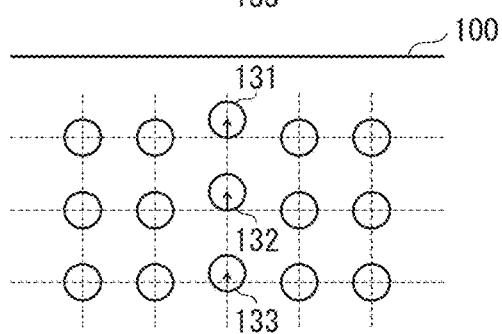
Figure 4D:
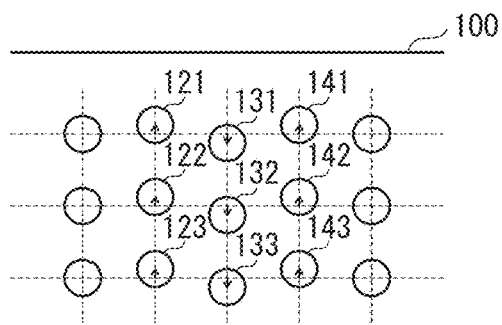
Figure 4E:
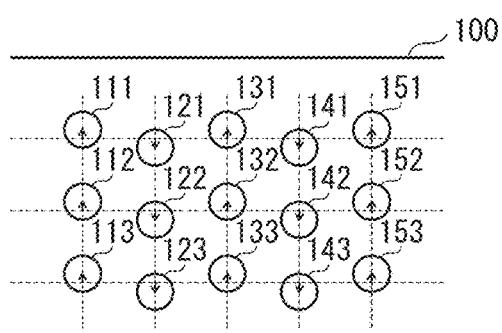

Here, a description is given of the generation of a shear wave using a push pulse with reference to a schematic diagram shown in FIGS. 4A to 4E. FIG. 4A is a schematic diagram showing a region of interest before a push pulse is applied. In FIGS. 4A to 4E, each "o" sign indicates a portion of the tissue inside the subject within the region of interest, and the intersections of the broken lines indicate the respective center points of the tissue portions when no load is applied. Here, when a push pulse is applied to a focal point 101 with the ultrasound probe 2 being in contact with a skin surface 100, as shown in the schematic diagram in FIG. 4B, a tissue portion 132 located at the focal point 101 moves in the travelling direction of the push pulse due to pressure. Also, a tissue portion 133, which is located in the travelling direction of the push pulse from the tissue portion 132, moves in the travelling direction of the push pulse due to pressure from the tissue portion 132. Next, upon completion of transmission of the push pulse, the tissue portions 132 and 133 make an attempt to return to their original positions, and accordingly, as shown in the schematic diagram in FIG. 4C, the tissue portions 131 to 133 start vibrating along the travelling direction of the push pulse. Consequently, as shown in the schematic diagram in FIG. 4D, the vibration propagates to tissue portions 121 to 123 and to tissue portions 141 to 143, which are adjacent to the tissue portions 131 to 133. Furthermore, as shown in the schematic diagram in FIG. 4E, the vibration further propagates to tissue portions 111 to 113 and to tissue portions 151 to 153. Thus, inside the subject, the vibration propagates in the direction that is perpendicular to the direction of vibration. In other words, a shear wave is generated at the position to which the push pulse is applied, and propagates inside the subject.

Returning to FIG. 3, the following provides a continuation of the description. Next, ultrasound is transmitted to and received from the region of interest a plurality of times, and a plurality of ultrasound signals thus obtained are stored (step S40). Specifically, the same operation as step S20 is performed for example 10000 times per second immediately after the completion of transmission of the push pulse. Consequently, cross-sectional images of the subject are repeatedly obtained during a period of time from immediately after the shear wave is generated to when the propagation ends.

Figure 5:
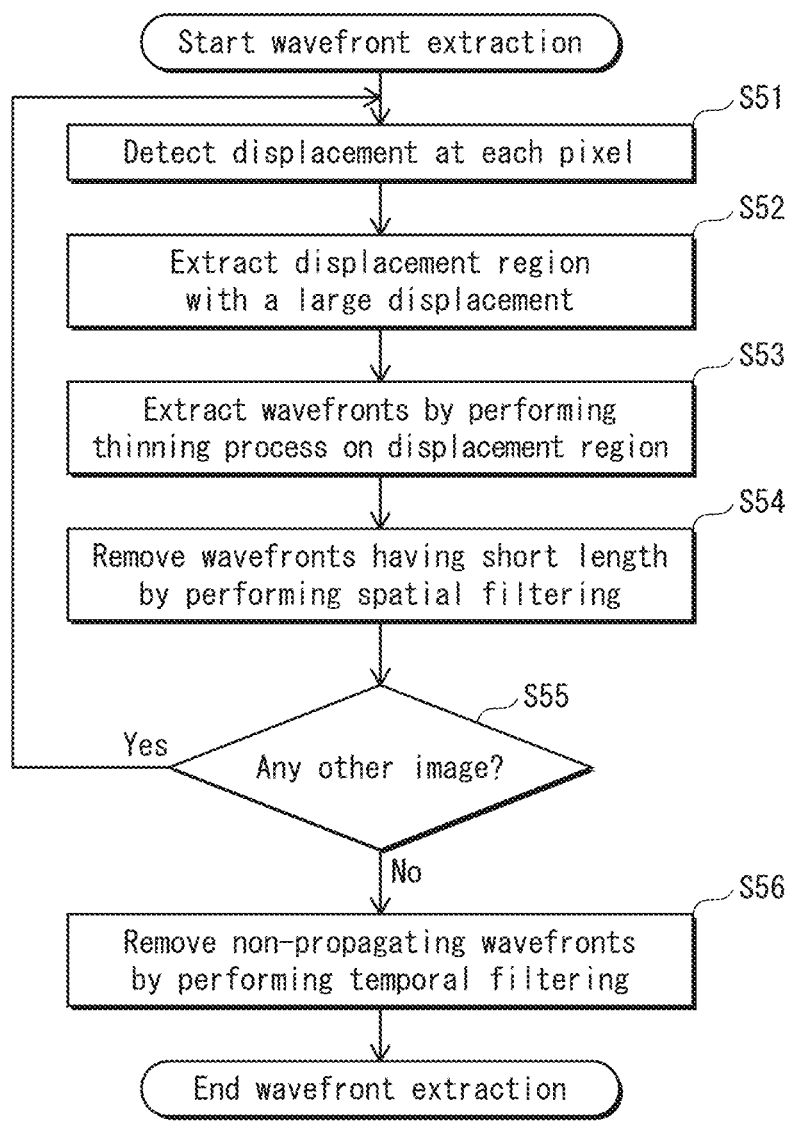
FIG. 5 is a flowchart showing wavefront extraction operations according to Embodiment 1.

Next, the wavefronts are extracted (step S50). Details are described below with reference to a flowchart shown in FIG. 5. FIG. 5 is a flowchart showing the details of wavefront extraction operations.

First, a displacement of each pixel is detected (step S51). Specifically, the displacement detector 14 obtains the cross-sectional image signals stored in the cross-sectional image storage 17 in step S20, which serve as reference cross-sectional image signals. As described above, the reference cross-sectional image signals are cross-sectional image signals that have been obtained before the emission of the push pulse, that is, before the generation of the shear wave. Next, the displacement detector 14 detects, with respect to each set of cross-sectional image signals stored in the cross-sectional image storage 17 in step S40, the displacement of each pixel at the time when the corresponding set of cross-sectional image signals were obtained, based on the differences from the set of reference cross-sectional image signals. Specifically, each set of cross-sectional image signals is divided into regions having a predetermined size such as 8 pixels×8 pixels, and the displacement of each of the pixels in each set of cross-sectional image signals is detected by performing pattern matching of the regions with the set of reference cross-sectional image signals. Consequently, how much the tissue portions of the subject, which correspond to the pixels in the set of cross-sectional image signals, have moved due to the push pulse or the shear wave is calculated as displacements. Note that the method for detecting the displacements is not limited to pattern matching, and any technique for detecting the amount of movement between two sets of cross-sectional image signals, such as a correlation process performed on a set cross-sectional image signals and the set of reference cross-sectional image signals, may be adopted. The displacement detector 14 generates a displacement image by associating the displacements of the pixels related to one cross-sectional image with the coordinates of the pixels, and outputs the displacement image thus generated to the displacement amount storage 18.

Figure 6A:
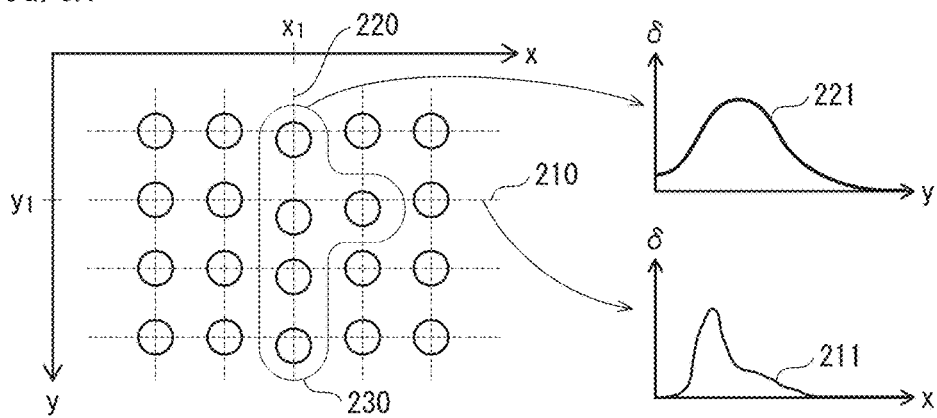
FIGS. 6A to 6E are schematic diagrams showing the wavefront extraction operations according to Embodiment 1.

Next, a displacement region with a large displacement is extracted (step S52). The displacement region extractor 31 obtains a displacement image from the displacement amount storage 18, and extracts a displacement region with a large displacement. The following provides a description with reference to the schematic diagrams shown in FIGS. 6A to 6E. FIG. 6A shows an example of the displacement image. As in FIGS. 4A to 4E, each "o" sign in the drawing indicates a portion of the tissue inside the subject within the region of interest, and the original positions of the tissue portions before the push pulse is applied coincide with the intersections of the broken lines. Also, the x axis indicates the direction in which the transducers are arranged, and the y axis indicates the depth direction of the subject. The displacement region extractor 31 extracts a region in which a displacement amount $\delta$ is large by using a dynamic threshold, where the displacement amount $\delta$ is a function of the x coordinate for each value of the y coordinate. The displacement region extractor 31 also extracts a region in which the displacement amount $\delta$ is large by using a dynamic threshold, where the displacement amount $\delta$ is a function of the y coordinate for each value of the x coordinate. Note that the dynamic threshold is a threshold that is determined by performing signal analysis or image analysis within the target region. The threshold is not a constant value, and varies depending on the width, the maximum value, etc., of the signals within the target region. FIG. 6A shows a graph 211, which is the plot of the displacement amount on a straight line 210 expressed by $y=y_1$, and a graph 221, which is the plot of the displacement amount on a straight line 220 expressed by $x=x_1$. With these graphs, a displacement region 230 whose displacement amount $\delta$ is greater than the threshold can be extracted, for example.

Figure 6B:
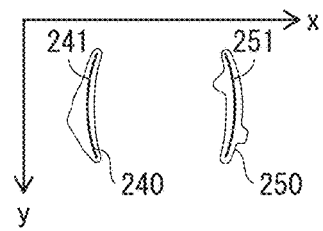
Figure 6C:
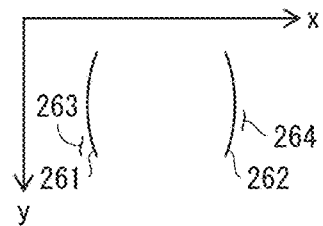
Figure 6D:
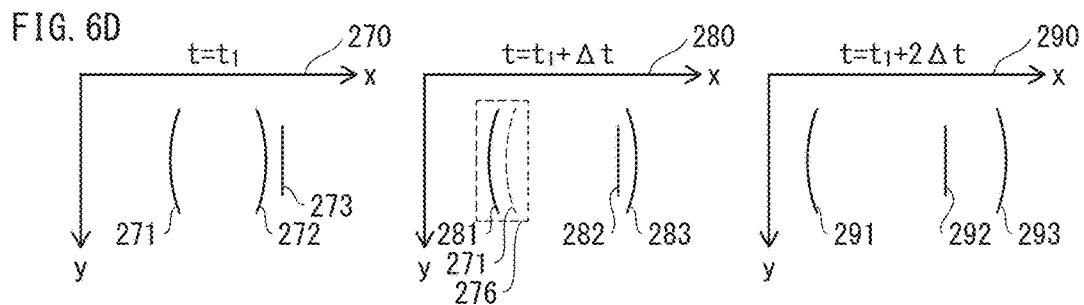
Figure 6E:
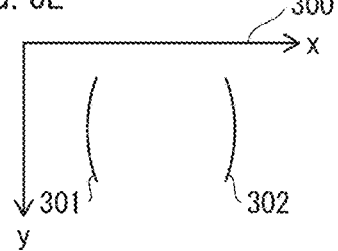
Figure 7A:
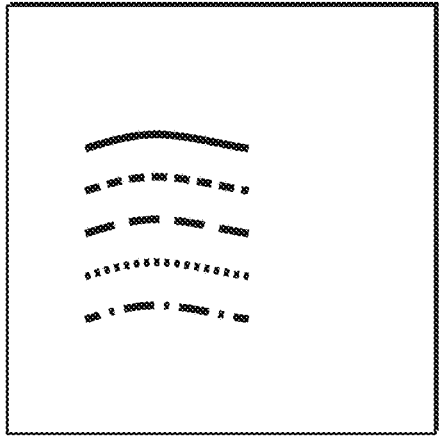
FIGS. 7A to 7E each show a display example of wavefronts according to Embodiment 1.
Figure 7B:
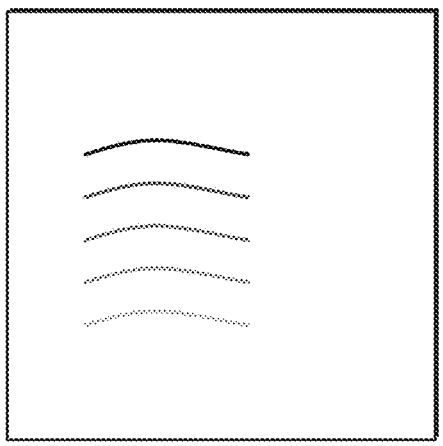
Figure 7C:
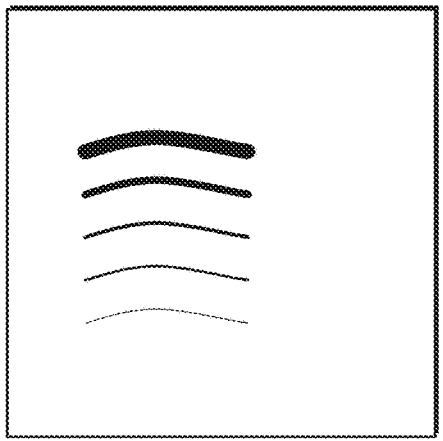
Figure 7E:
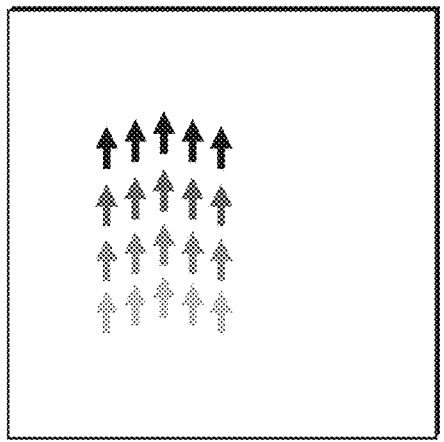
Figure 7D:
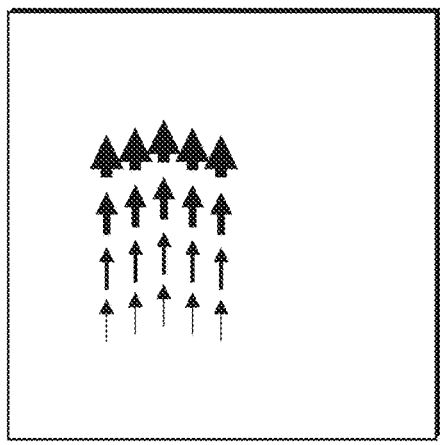

Next, the thinner 32 performs a thinning process on the displacement region, thereby extracting wavefronts (step S53). Displacement regions 240 and 250 shown in the schematic diagram in FIG. 6B are each a region extracted in step S52 as a displacement region. The thinner 32 extracts wavefronts by using Hilditch's thinning algorithm, for example. For example, in the case of the schematic diagram shown in FIG. 6B, a wavefront 241 is extracted from the displacement region 240, and a wavefront 251 is extracted from the displacement region 250. Note that the thinning algorithm is not limited to that of Hilditch, and any thinning algorithm may be adopted. Also, the process of removing coordinates whose displacement amount $\delta$ is smaller than or equal to the threshold from the displacement region may be repeatedly performed on each displacement region with the threshold gradually increased until the displacement region becomes a line having a width of one pixel. The thinner 32 outputs the extracted wavefronts, which serve as wavefront image data, to the spatial filter 33.

Next, the spatial filter 33 performs spatial filtering on the wavefront image data generated by the thinner 32, thereby removing wavefronts having a short length (step S54). For example, the spatial filter 33 detects the length of each wavefront extracted in step S53, and removes wavefronts having a length that is shorter than half the average value of the lengths of all the wavefronts, regarding them as noise. Specifically, as shown in the wavefront image in FIG. 6C, the spatial filter 33 calculates the average value of the lengths of wavefronts 261 to 264, and removes the wavefronts 263 and 264 having a length that is shorter than the average value, regarding them as noise. Wavefronts that have been erroneously detected can be thus removed.

The wavefront extractor 15 performs the operations in steps S51 to S54 for every displacement image (step S55). Thus, pieces of wavefront image data are generated in one-to-one correspondence with the displacement images.

Next, the temporal filter 34 performs temporal filtering on the pieces of wavefront image data, thereby removing non-propagating wavefronts (step S56). Specifically, the temporal filter 34 detects temporal changes in the wavefront positions from two or more wavefront images that are temporally successive, and removes wavefronts with an abnormal speed, regarding them as noise. The wavefront extractor 15 detects temporal changes in the wavefront positions, for example between a wavefront image 270 at time t=$t_1$, a wavefront image 280 at time t=$t_1$+Δt, and a wavefront image 290 at time t=$t_1$+2Δt. For example, regarding the wavefront 271, the wavefront extractor 15 performs the correlation process with the wavefront 271 in a region 276 that is a region centered around the same position as the wavefront 271 in the wavefront image 280, within which the shear wave can travel during a period of time Δt in the direction that is perpendicular to the wavefronts (the x axis direction in FIGS. 6A to 6E). Here, the correlation process is performed within a range that includes both the positive x axis direction (to the right side of the drawing) and the negative x axis direction (to the left side of the drawing) of the wavefront 271. This is for the purpose of detecting both transmitted waves and reflected waves. Consequently, the wavefront extractor 15 detects that the destination wavefront to which the wavefront 271 has travelled is a wavefront 281 within the wavefront image 280, and calculates the moving distance of the wavefront 271 during the period of time Δt. Similarly, regarding each of the wavefronts 272 and 273, the wavefront extractor 15 performs the correlation process in a region centered around the same position as the corresponding wavefront in the wavefront front image 280, within which the shear wave can travel during the period of time Δt in the direction that is perpendicular to the wavefronts. Consequently, the wavefront extractor 15 detects that the wavefront 272 has travelled to the position of the wavefront 283, and the wavefront 273 has travelled to the position of the wavefront 282. The wavefront extractor 15 performs the same process between the wavefront image 280 and the wavefront image 290 as well, and detects that the wavefront 281 has travelled to the position of a wavefront 291, the wavefront 282 has travelled to the position of a wavefront 292, and the wavefront 283 has travelled to the position of a wavefront 293. Here, the single wavefront indicated by the wavefront 273, the wavefront 282, and the wavefront 292 has a significantly small travelling distance (a significantly low propagation speed) compared to other wavefronts. It is likely that such a wavefront is an erroneously detected wavefront, and thus the wavefront is removed as noise. Consequently, wavefronts 301 and 302 are detected as shown in a wavefront image 300 in FIG. 6E.

By these operations, a wavefront image data piece can be generated for each point in time. The wavefront extractor 15 outputs the pieces of wavefront image data thus generated to the wavefront image storage 19. At this time, waveform correspondence information for the pieces of wavefront image data thus generated may also be output to the wavefront image storage 19. Waveform correspondence information is information indicating wavefronts that the same wavefront corresponds to in each wavefront image. For example, when it is detected that the wavefront 272 has travelled to the position of the wavefront 283, the waveform correspondence information indicates that the wavefront 283 and the wavefront 272 correspond to the same wavefront.

Returning to FIG. 3, the following provides a continuation of the description. Next, the wavefront image processor 16 modifies the mode of displaying the wavefronts (step S60). Specifically, the wavefront image processor 16 changes the mode of displaying the wavefronts in each piece of wavefront image data such that wavefronts at the same point in time are displayed in the same mode. FIGS. 7A to 7E show examples of the modes of displaying wavefronts. Note that in FIGS. 7A to 7E, a plurality of wavefront images at different points in time, which have been superposed and combined with each other, are displayed. As shown in the display example in FIG. 7A for example, the thickness of the lines indicating wavefronts may be varied for each point in time. Alternatively, as shown in the display example in FIG. 7B for example, the luminance of the lines indicating the wavefronts may be varied for each point in time. Note that the color of the lines indicating wavefronts, or both the color and the luminance of the lines indicating wavefronts may be varied for each point in time. In this regard, in a wavefront image at a given point in time for example, it is acceptable that wavefronts at the given point in time are displayed in the color red, and wavefronts at other points in time (which may be all the other points in time, all the points in time that are before the given point in time, or a specific number of points in time before the given point in time) are displayed in the color black and superposed and combined with the wavefront image. Note that the colors red and black are merely examples, and of course any other colors may be adopted. The configuration above makes it easy to check the wavefronts travelling and also the paths of travel of the wavefronts. Also, as shown in the display example in FIG. 7C for example, the line type, such as a solid line, a broken line, or a dot-and-dash line, may be varied for each point in time. Note that the display modes above may be combined, and, for example, the thickness and the type of the lines expressing the wavefronts may be varied. Also, the display modes of the wavefronts are not limited to modes in which the wavefronts are expressed as lines, and as shown in the display example in FIG. 7D for example, one wavefront may be expressed as a plurality of arrows of the same type, and the display mode of the arrows may be varied for each point in time. Here, techniques of varying the display mode of the arrows include, for example, the technique of varying the thickness of the arrows as shown in the display example in FIG. 7D, the technique of varying the luminance and the color of the arrows as shown in the display example in FIG. 7E, and the technique of varying the length of the arrows. In the case of expressing a wavefront as an arrow, it is possible to make the travelling direction and the propagation speed of the wavefront clearer by expressing the travelling direction of the wavefront as the orientation of the arrow, and expressing the propagation speed of the wavefront as the length of the arrow. Note that the travelling directions and the propagation speeds of a wavefront can be obtained from the movement of the wavefront in two wavefront images that are temporally successive. In other words, in two wavefront images that are temporally successive, the moving direction of a wavefront indicates the travelling direction of the wavefront, and the moving distance of the wavefront indicates the propagation speed of the wavefront.

Finally, the controller 11 displays the wavefronts in the form of a moving image (step S70). Specifically, the controller 11 performs geometric conversion on the pieces of wavefront image data modified by the wavefront image processor 16 to form image data to be displayed on the screen, and successively displays the pieces of wavefront image data, which have undergone geometric conversion, on the display 3.

Examples of Wavefront Images

The following shows examples of wavefronts in the case where a shear wave passes through a tissue that contains a hard inclusion.

FIGS. 8A to 8H show examples of wavefront images showing passage and reflection of a shear wave. FIGS. 8A to 8H sequentially show the propagation of a shear wave that propagates from the left to the right of each drawing. Note that although FIGS. 8A to 8H show an inclusion 320 that is harder than surrounding tissues, only a wavefront 310, or wavefronts 311 and 312 are depicted in each wavefront image.

When the hardness of the tissue is approximately uniform as shown in FIGS. 8A to 8C, the propagation speed of the shear wave is approximately constant, and accordingly the wavefront 310 propagates with approximately no change in the shape. When the shear wave reaches the surface of the hard inclusion 320, a transmitted wave travels through the inside of the inclusion 320, and also a reflected wave is generated at the surface of the inclusion 320 as shown in FIG. 8D. FIG. 8D shows the wavefront 311 of the transmitted wave and the wavefront 312 of the reflected wave. Here, regarding the transmitted wave, the propagation speed of the shear wave increases as the hardness of the tissue increases. Therefore, the wavefront 311 travels through the inside of the inclusion 320 at a high speed, and the shape of the wavefront changes as shown in FIGS. 8E to 8G. In the drawings, the inclusion 320 has the shape of a circle, and since the distance that the wavefront travels through the inside of the inclusion 320 varies depending on the depth, the wavefront has a shape that protrudes in the travelling direction. Note that regarding the protrusion of the transmitted wave in the travelling direction of the wavefront 311, the shape of the wavefront 311 of the transmitted wave does not change after the shear wave has travelled to the outside of the inclusion 320 again because the propagation speed of the shear wave is thereafter constant. On the other hand, since the reflected wave is generated when the wavefront 311 of the transmitted wave comes into contact with the surface of the inclusion 320, the wavefront 312 of the reflected wave is formed so as to radially spread from the left-half region of the surface of the inclusion 320. Therefore, as shown in FIGS. 8E to 8G, the length of the wavefront 312 of the reflected wave increases as the distance from the inclusion 320 increases.

Conclusion

The configuration above makes it possible to check how the shear wave generated by the push pulse has propagated. Therefore, it is possible to determine whether the shear wave has propagated from the position to which the push pulse was applied without being reflected for example, or the shear wave has been reflected by the inclusion or the like, and thus the examiner can determine whether or not the results of measurement of the hardness of the tissue are reliable. Also, in the case where the shear wave has been reflected and the examiner has been unable to obtain the hardness of the tissue, the examiner can see that the results of measurement of the hardness of the tissue are not reliable, and also see how the shear wave has propagated. Accordingly, the examiner can see the position and the approximate shape of the inclusion that has generated the reflection of the shear wave, and can change the position to which the push pulse is applied, so as to reduce the influence of the reflection of the shear wave. Therefore, the examiner can perform re-examination after taking measures to make it possible to obtain the results with a high probability.

Modified Example 1

In Embodiment 1, a description has been given of the case of extracting a displacement region with a large displacement from each displacement image, detecting wavefronts, and performing filtering based on temporal changes in the wavefront images. In contrast, the present modified example is characterized by detecting wavefronts based on temporal changes in the displacement at each of several positions within a tissue.

Configuration

Figure 9:
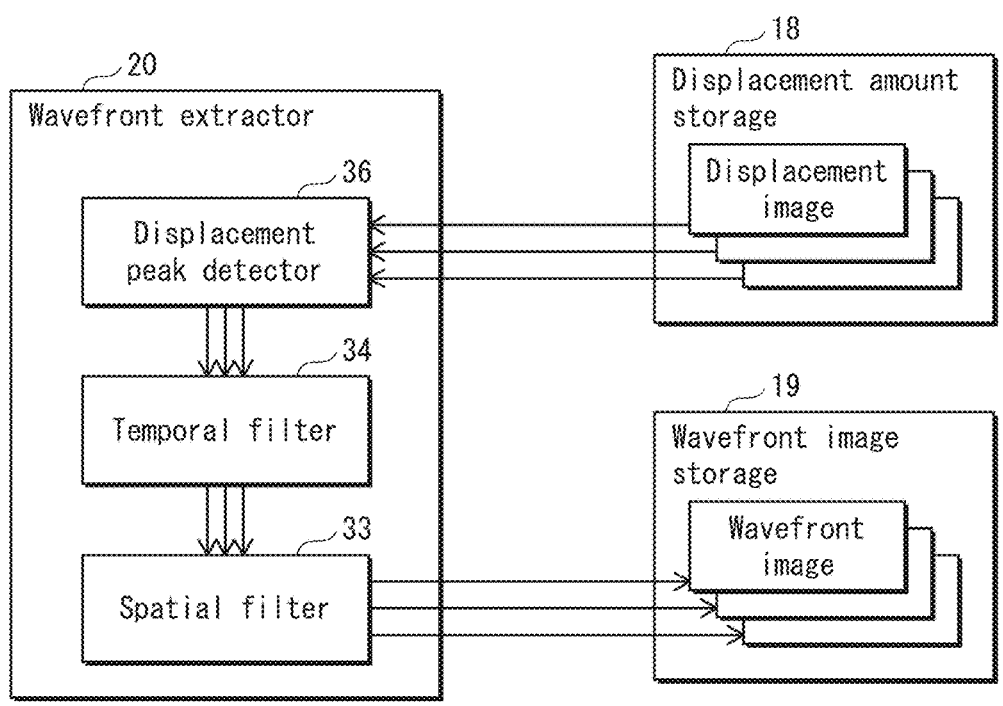
FIG. 9 is a functional block diagram of a wavefront extractor 20 according to Modified Example 1.

FIG. 9 is a functional block diagram of a wavefront extractor 20 according to the present modified example. As shown in FIG. 9, the wavefront extractor 20 includes a displacement peak detector 36, the temporal filter 34, and the spatial filter 33. The displacement peak detector 36 calculates, for each coordinate point, the point in time at which the amount of displacement reaches its peak, based on temporal changes in the displacement at the corresponding coordinate point in the displacement images. Based on the points in time thus calculated, the displacement peak detector 36 calculates the displacement region with a large displacement at each point in time, and generates wavefront image data by extracting each displacement region as a wavefront. The temporal filter 34 performs temporal filtering on the wavefront image data. The spatial filter 33 performs spatial filtering on the wavefront image that has undergone temporal filtering.

Note that the configuration of the ultrasound diagnostic device according to the present modified example is the same as the configuration of the ultrasound diagnostic device 1 except that the wavefront extractor 20 is provided in place of the wavefront extractor 15, and therefore the components shared with the ultrasound diagnostic device 1 are not described below.

Operations

Figure 10:
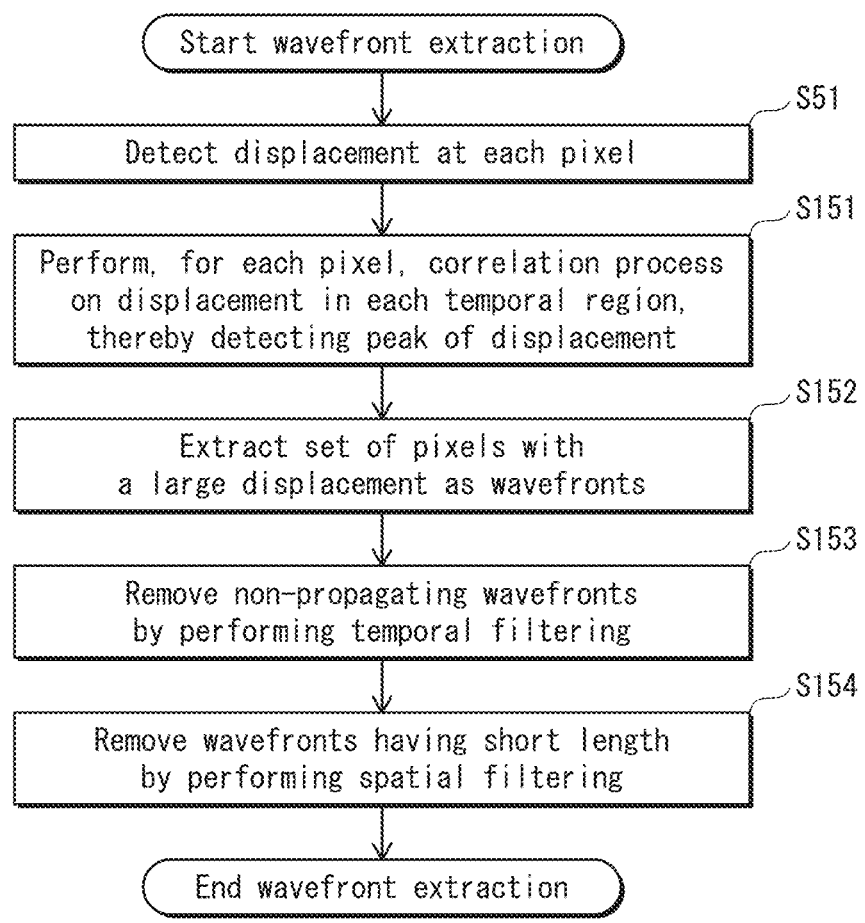
FIG. 10 is a flowchart showing wavefront extraction operations according to Modified Example 1.

FIG. 10 is a flowchart showing wavefront extraction operations according to the present modified example. Note that the operations of the ultrasound diagnostic device according to the present Modified Example 1 are different from those of the ultrasound diagnostic device 1 according to Embodiment 1 in terms of the wavefront extraction operations described below, and other operations are not described below because they are the same as those of the ultrasound diagnostic device 1.

First, a displacement at each pixel is detected (step S51). Specific operations are not described below because they have been described in Embodiment 1. The displacement detector 14 generates displacement images by associating the displacements of the pixels related to one corresponding cross-sectional image with the coordinates of the pixels, and outputs the displacement images thus generated to the displacement amount storage 18.

Figure 11A:
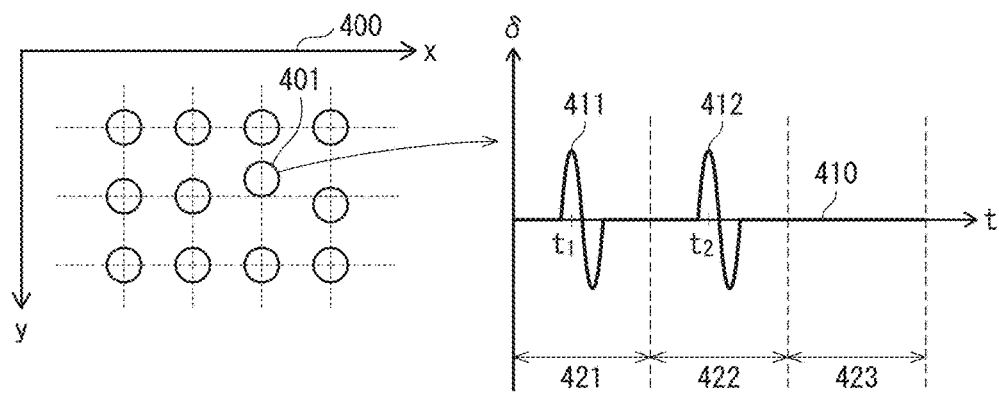
FIGS. 11A to 11E are schematic diagrams showing the wavefront extraction operations according to Modified Example 1.
Figure 11B:
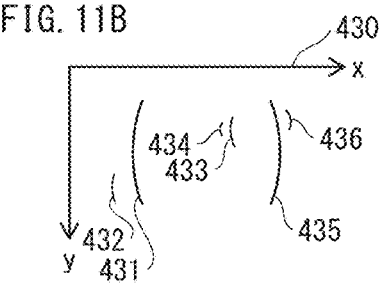
Figure 11C:
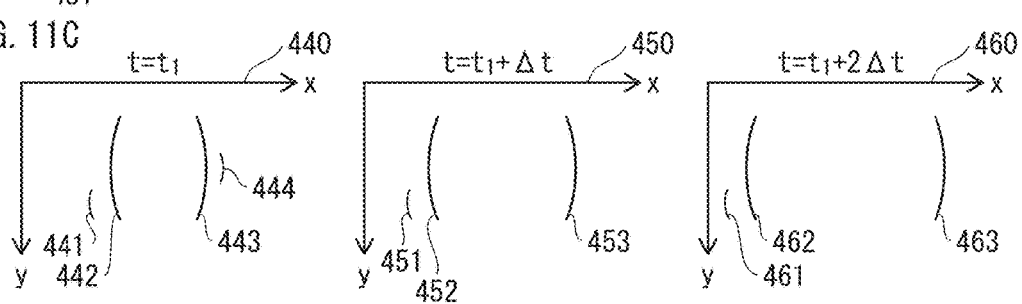
Figure 11D:
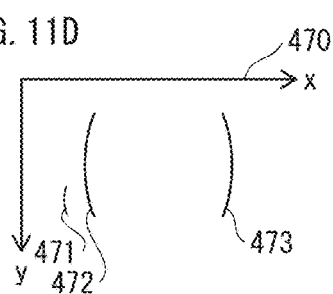

Next, the displacement detector 14 performs, for each pixel, the correlation process on the displacement in each temporal region, thereby detecting the peak of the displacement (step S151). The displacement peak detector 36 obtains the displacement images from the displacement amount storage 18. The following provides a description with reference to the schematic diagrams shown in FIGS. 11A to 11E. FIG. 11A shows an example of the displacement image. As in FIGS. 4A to 4E and FIG. 6A, each "o" sign in the drawing indicates a portion of the tissue inside the subject within the region of interest, and the original positions of the tissue portions before the push pulse is applied coincide with the intersections of the broken lines. Also, the x axis indicates the direction in which the transducers of the ultrasound probe 2 are arranged, and the y axis indicates the depth direction of the subject. The displacement peak detector 36 detects, for each coordinate point, the points in time at which the displacement amount δ takes its extremum. Here, the extremum refers to the maximum value and the minimum value (the displacement amount δ is a negative value and its absolute value is the maximum value). In the present modified example, it is assumed that the displacement peak detector 36 detects only the point in time at which the displacement amount δ takes the maximum value (the displacement amount δ is a positive value). A graph 410 in FIG. 11A shows the displacement amount δ at a point 401 with coordinates $(x_1, y_1)$ as a function of time t. Note that since the displacement amount δ here is treated as a one-dimensional vector, the displacement amount δ is a value that indicates only a displacement in the y axis direction, and the displacement in the direction of increasing depth (the direction of rise in the y coordinate) is expressed as a positive value, and the displacement in the direction of decreasing depth (the direction of decrease in the y coordinate) is expressed as a negative value. The wavefront extractor 20 divides the period of time during which the cross-sectional image signals have been obtained into a plurality of sections 421, 422, and 423. The wavefront extractor 20 then performs the correlation process with respect to each of the displacement amount δ in the section 421, the displacement amount δ in the section 422, and the displacement amount δ in the section 423, thereby detecting the points in time $t_1$ and $t_2$ at which the displacement amount δ peaks. Here, the period of time during which the cross-sectional image signals have been obtained is divided into a plurality of sections because there is the possibility of a wavefront passing through the region of interest a plurality of times, for example in the case where a reflected wave passes through the region of interest. Note that although only the point in time at which the displacement amount δ takes the maximum value is detected in the present modified example, the point in time at which the correlation value obtained by the correlation process is a negative value and its absolute value is the maximum value, i.e., the point in time at which the displacement amount δ is a negative value and its absolute value is the maximum value, may also be detected. Such a modification makes it possible to also detect a wavefront having an inverted phase.

Next, a set of pixels with a large displacement is extracted as a wavefront (step S152). Specifically, the displacement peak detector 36 obtains, for each point in time, a set of points at which the displacement amount δ peaks as a displacement region, and extracts each displacement region as a wavefront. That is, as shown in a wavefront image 430 in FIG. 11B, for the point in time t1, a displacement region 431 that includes a point with coordinates $(x_1, y_1)$, and displacement regions 432, 433, 434, 435, and 436 are each extracted as a wavefront. Note that, as described above, a phase-inverted wavefront, which has a phase that is the inversion of the phase of the detected phase above, may also be extracted based on a set of pixels at which the displacement amount δ is a negative value and its absolute value is the maximum value. The displacement peak detector 36 outputs the extracted wavefronts, which serve as wavefront image data for each point in time, to the temporal filter 34.

Next, the temporal filter 34 performs temporal filtering on the pieces of wavefront image data, thereby removing non-propagating wavefronts (step S153). Specifically, in the same manner as in step S56 according to Embodiment 1, the temporal filter 34 detects temporal changes in the wavefront positions from two or more wavefront images that are temporally successive, and removes wavefronts with an abnormal speed, regarding them as noise. The wavefront extractor 20 detects temporal changes in the wavefront positions, for example between a wavefront image 440 at time $t=t_1$ and a wavefront image 450 at time $t=t_1+\Delta t$, and between the wavefront image 450 at time $t=t_1+\Delta t$ and a wavefront image 460 at time $t=t_1+2\Delta t$. Detection of temporal changes in the wavefront positions is, in the same manner as in step S56, achieved by, for example, performing the correlation process with respect to each wavefront in the wavefront image 440, within a region centered around the same position as the corresponding wavefront in the wavefront front image 450, within which the shear wave can travel during the period of time Δt in the direction that is perpendicular to the wavefronts. For example, between the wavefront image 440 and the wavefront image 450, the wavefront extractor 20 detects that a wavefront 441 has travelled to the position of a wavefront 451, a wavefront 442 has travelled to the position of a wavefront 452, and a wavefront 443 has travelled to the position of a wavefront 453. Here, the destination wavefront to which the wavefront 444 has travelled is not detected for the following reason. In the correlation process between a wavefront image X including a wavefront A and a wavefront B, and a wavefront image Y including a wavefront C, in the case where a region centered around the wavefront A and a region centered around the wavefront B in the wavefront image Y overlap each other and the wavefront C exists in the overlapping region, the destination wavefront is determined in the following manner. The correlation value between the wavefront A and the wavefront C and the correlation value between the wavefront B and the wavefront C are each calculated, and (1) when only one of the correlation values is higher than or equal to a threshold, whichever one of the wavefront A and the wavefront B has a correlation value with the wavefront C that is higher than or equal to the threshold is regarded as the wavefront that travelled to the wavefront C, and (2) when both correlation values are higher than or equal to the threshold, whichever one of the wavefront A and the wavefront B has a higher correlation value with the wavefront C than the correlation value of the other is regarded as the wavefront that travelled to the wavefront C, and (3) when both correlation values are lower than the threshold, it is determined that neither of them is a wavefront that travelled to the wavefront C. The wavefronts 442, 443, 452, and 453 have substantially the same length, whereas the wavefront 444 has a length that is much shorter than that of the other wavefronts. Therefore, the correlation value between the wavefront 443 and the wavefront 453 is higher than the correlation value between the wavefront 444 and the wavefront 453. For this reason, in a region centered around the same position as the wavefront 444 in the wavefront image 450, there is no destination wavefront to which the wavefront 444 has travelled. The wavefront 444, which has no destination wavefront, is removed as noise. Similarly, between the wavefront image 450 and the wavefront image 460, the wavefront extractor 20 detects that the wavefront 451 has travelled to the position of a wavefront 461, the wavefront 452 has travelled to the position of a wavefront 462, and the wavefront 453 has travelled to the position of a wavefront 463. The temporal filter 34 outputs the wavefront image data that has undergone temporal filtering to the spatial filter 33. Note that as described in Embodiment 1, the temporal filter 34 may also output waveform correspondence information to the spatial filter 33.

Figure 11E:
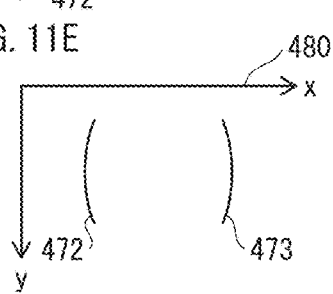

Next, the spatial filter 33 performs spatial filtering on the wavefront image data that has undergone time filtering, thereby removing wavefronts having a short length (step S154). Specifically, as in step S54 according to Embodiment 1, the spatial filter 33 detects the lengths of wavefronts in each wavefront image, and removes wavefronts having a length that is shorter than half the average value of the lengths of all the wavefronts, regarding them as noise. Specifically, as shown in a wavefront image 470 in FIG. 11D, the spatial filter 33 calculates the average value of the lengths of wavefronts 471 to 473, and removes the wavefront 471 having a length that is shorter than the average value, regarding it as a noise. Wavefronts that have been erroneously detected can be thus removed. Note that in the case where the spatial filter 33 has received wavefront correspondence information, the spatial filter 33 may collectively remove wavefronts that are the same as the wavefronts that have been removed, from other wavefront images. As shown in FIG. 11E, only the wavefronts 472 and 473 remain in the wavefront image 480 that has undergone spatial filtering.

The wavefront extractor 20 outputs the pieces of wavefront image data that have undergone spatial filtering to the wavefront image storage 19. Note that the wavefront extractor 20 may also output wavefront correspondence information.

Conclusion

In the present modified example, a description has been given of the case of detecting wavefronts based on temporal changes in the displacement at each of several positions within a tissue. Since the peak of a displacement in a time series is detected for each coordinate point, displacements without a temporal change are not detected, which makes it possible to avoid erroneously detecting noise in the reference cross-sectional image signals, or noise without a temporal change caused by, for example, a positional mismatch between the reference cross-sectional image signals and the cross-sectional image signals, as displacements. Also, since the peak of a displacement in a time series is detected for each coordinate point a plurality of times, wavefronts can be extracted even in the case where a wavefront passes through a single place a plurality of times, especially in the case where a transmitted wave and a reflected wave pass through the same place. Also, when detecting the peak of a displacement in a time series for each coordinate point, detecting the point in time at which the correlation value is a negative value and its absolute value is the maximum value makes it possible to detect a wavefront having an inverted phase in the case where the phase of the shear wave has been inverted, and to detect a reflected wavefront in the case where a shear wave that is likely to undergo fixed end reflection has been reflected.

Modified Example 2

In Embodiment 1 and Modified Example 1, no difference is made between the mode of displaying a transmitted wave and the mode of displaying a reflected wave. The present modified example is characterized by making a difference between the mode of displaying a transmitted wave and the mode of displaying a reflected wave, or displaying either one of them alone.

Wavefront Classification Operations

In the present modified example, wavefronts are classified as the wavefront of a transmitted wave or the wavefront of a reflected wave. Here, a transmitted wave is a wave that is generated by application of a push pulse, and propagates while travelling away from the position where the push pulse was applied. On the other hand, a reflected wave is a reflection of a transmitted wave that has been reflected inside the subject, and propagates differently from a transmitted wave.

Figure 12:
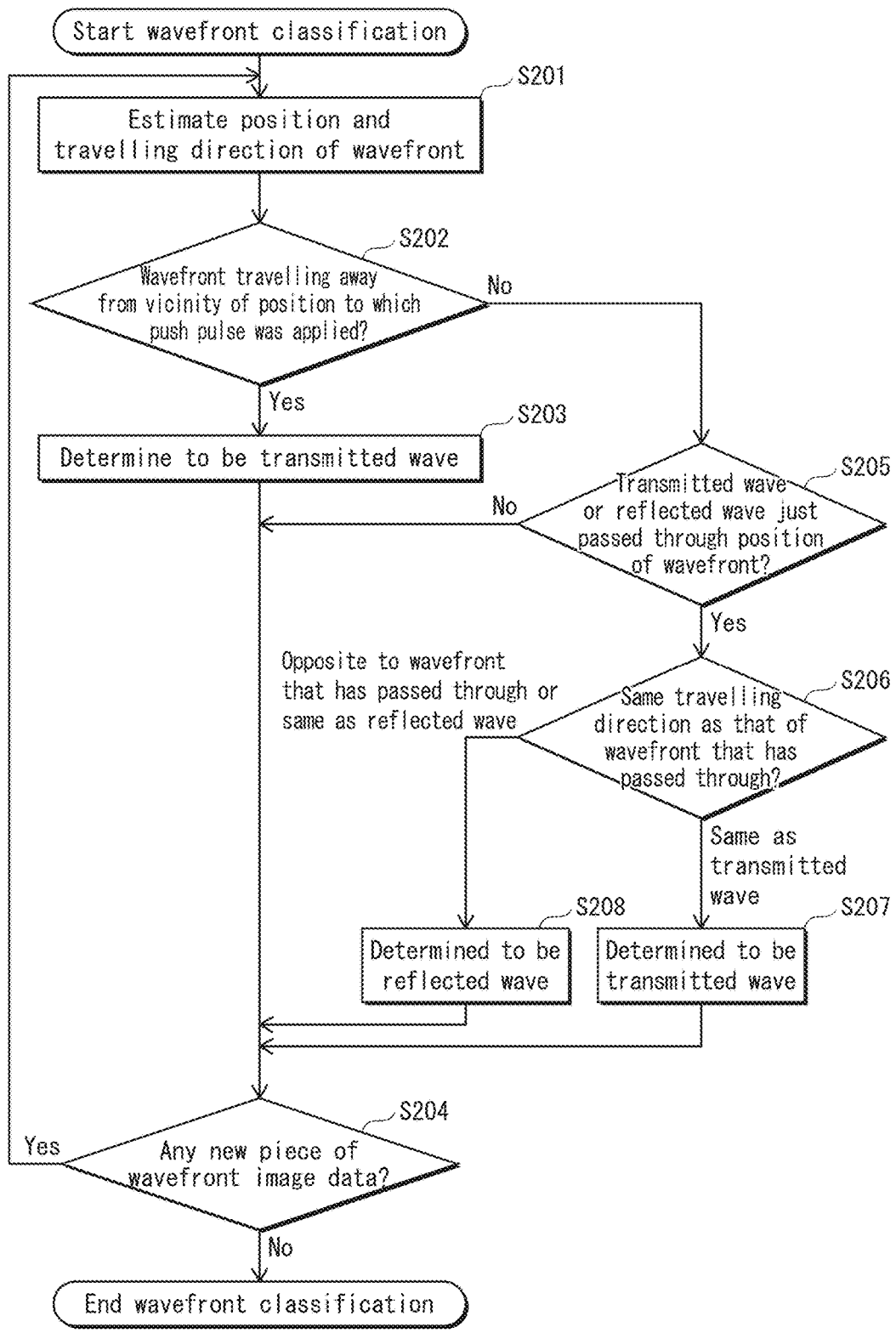
FIG. 12 is a flowchart showing wavefront classification operations according to Modified Example 2.

FIG. 12 is a flowchart showing wavefront classification operations. First, with respect to each wavefront in the wavefront image that was obtained at the earliest point in time, the position and the travelling direction of the wavefront are estimated (step S201).

Next, a determination is made as to whether or not the wavefront is travelling away from the vicinity of the position where the push pulse was applied (step S202). Specifically, a determination is made as to whether or not the wavefront satisfies all of the following conditions: (1) the position of the wavefront is in the vicinity of the position to which the push pulse was applied; (2) the point in time at which the wavefront image was obtained is immediately after, or within a predetermined period of time from, the point in time at which the push pulse was applied; and (3) the wavefront is travelling away from the position to which the push pulse was applied. In the case where all of the conditions are satisfied, the wavefront can be assumed to be the wavefront of the shear wave that has been generated by the push pulse, and thus the wavefront is determined to be the wavefront of a transmitted wave (step S203), and the process proceeds to step S204. On the other hand, in the case where any of the conditions is not satisfied, the process proceeds to step S205, which is the subsequent determination step.

In step S205, a determination is made as to whether or not a transmitted wave or a reflected wave (each hereinafter referred to as "a reference wavefront") has just passed through the position of the wavefront. A reference wavefront is specifically a wavefront that exists at the position of a wavefront that is to be subjected to classification and that is contained in the wavefront image that was obtained immediately before the point in time at which the wavefront image of interest was obtained, or in the wavefront image that was obtained at a point in time that is before the aforementioned point in time and within a predetermined range of the aforementioned point in time. In the case where there is a reference wavefront, the wavefront concerned can be assumed to be a wavefront that is the same as the reference wavefront, or a wavefront that was generated due to the reference wavefront, and therefore the process proceeds to step S206, which is the subsequent determination step. On the other hand, in the case where there is no reference wavefront, the type of the wavefront cannot be specified, and therefore the process proceeds to step S204, with the type of the wavefront remaining unclassified.

In step S206, a determination is made as to whether the travelling direction of the wavefront and that of the reference wavefront are substantially the same or opposite. In the case where the travelling direction of the wavefront and that of the reference wavefront are substantially the same, the wavefront and the reference wavefront can be assumed to be the same wavefronts, and therefore the wavefront is classified into the same type as the reference wavefront. That is, when the reference wavefront is the wavefront of a transmitted wave, the wavefront concerned is determined to be the wavefront of a transmitted wave (step S207), and when the reference wavefront is the wavefront of a reflected wave, the wavefront concerned is determined to be the wavefront of a reflected wave (step S208). On the other hand, in the case where the travelling direction of the wavefront and that of the reference wavefront are opposite, the wavefront can be assumed to be a reflection of the reference wavefront reflected at the location of generation, and therefore the wavefront is determined to be the wavefront of a reflected wave (step S208). The type of the wavefront has been thus determined, and the process then proceeds to step S204.

In step S204, a determination is made as to whether or not there is wavefront image data that was obtained at the next point in time. In the case where there is such wavefront image data, the process returns to step S201 and the wavefront in the wavefront image obtained at the next point in time is subjected to classification. In the case where there is no such wavefront image data, the process ends.

Figure 13C:
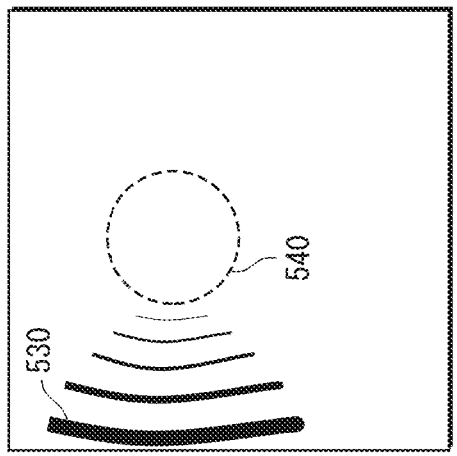
FIGS. 13A to 13E each show an example of a wavefront image according to Modified Example 2.
Figure 13B:
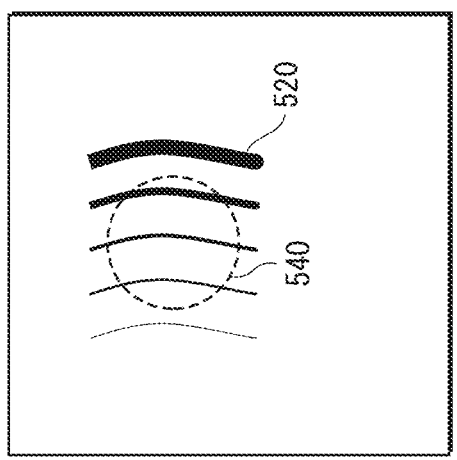
Figure 13A:
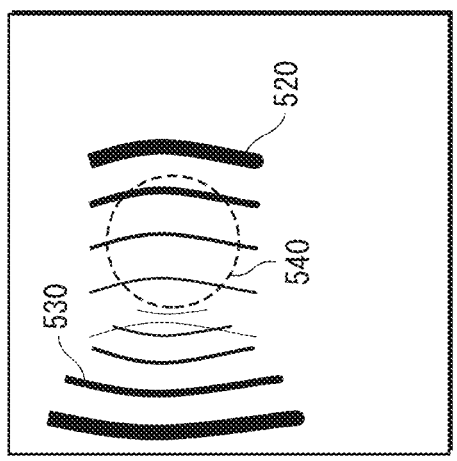
Figure 13E:
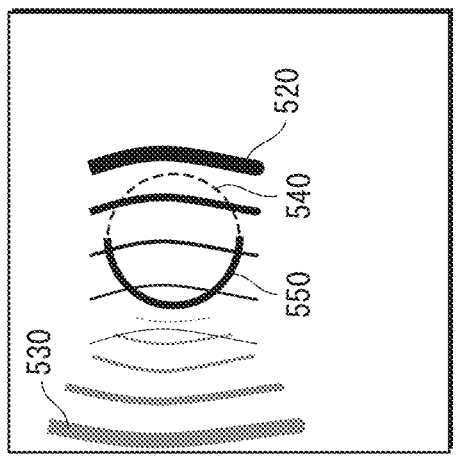
Figure 13D:
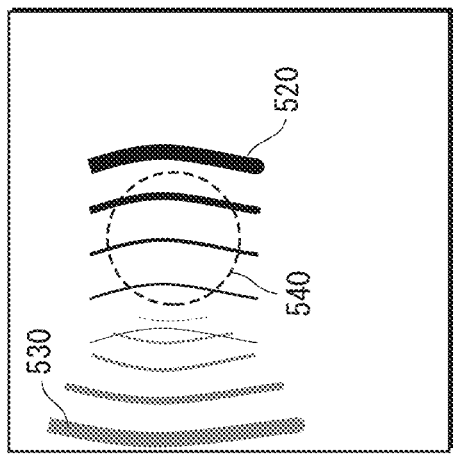

As described above, wavefronts are classified as the wavefront of a transmitted wave or the wavefront of a reflected wave, which makes it possible to display either a set of wavefronts of transmitted waves or a set of wavefronts of reflected waves alone, or to display each set in a different mode. For example, in the wavefront image shown in FIG. 13A, both the transmitted wave 520 and the reflected wave 530 are displayed with no difference between them. However, the transmitted wave 520 may be displayed alone as is in the wavefront image shown in FIG. 13B, or the reflected wave 530 may be displayed alone as is in the wavefront image shown in FIG. 13C. In FIGS. 13A to 13E, an inclusion 540 is the cause of generation of the reflected wave 530. However, the inclusion 540 is shown for the purpose of explanation, and the inclusion 540 cannot be seen directly on the wavefront image. In addition, as shown in FIG. 13D, the display mode may be varied for the transmitted wave 520 and the reflected wave 530, with respect to the luminance and the color, for example. Note that the display mode may be related to the type and the thickness of lines as well as the luminance and the color, and alternatively, transmitted waves and reflected waves may be respectively displayed as lines and arrows. Also, as shown in FIG. 13E, a reflection boundary 550 may be shown. Note that the reflection boundary 550 can be detected by, when it is determined in step S206 that the travelling direction of the wavefront and that of the reference wavefront are opposite, storing the location of generation of the wavefront, and accumulating the location of generation of every reflected wave.

Conclusion

In the present modified example, a description has been given of the case of making a difference between the mode of displaying transmitted waves and the mode of displaying reflected waves, or displaying either one of them alone. With such a configuration, in the case where reflection of the shear wave occurs, it is possible to display only the reflected wave so as to be able to check the reflection boundary, the location where the speed of the shear wave could not be obtained due to the reflected wave, and the like, and it is also possible to avoid the situation where it is difficult to check the propagation state of transmitted waves due to interference of transmitted waves and reflected waves with each other. Thus, the present modified example makes it possible to provide the examiner with more accurate information about the locations of generation of reflected waves and the propagation states of transmitted waves.

Modified Example 3

In Embodiment 1 and Modified Examples 1 and 2, the case of transmitting a push pulse only once to only one place is described. In contrast, the present modified example describes the case of transmitting a push pulse twice, i.e., to a plurality of places.

In the case of transmitting a push pulse to two places, the push pulse may be transmitted to two places in a single instance of transmission in step S20. Alternatively, it is acceptable that an ultrasound signal is obtained as in step S30 after the push pulse is transmitted for the first time, and then an ultrasound signal is obtained again as in step S30 after the push pulse is transmitted for the second time.

Figure 14A:
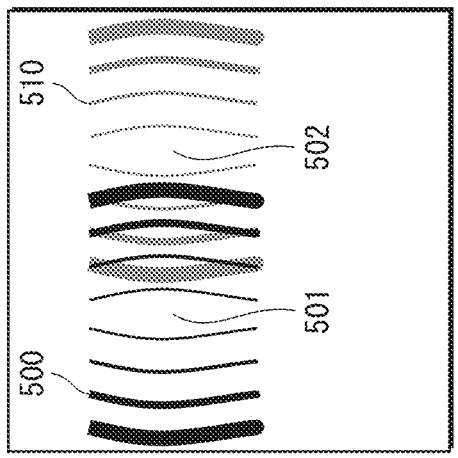
FIGS. 14A to 14C each show an example of a wavefront image according to Modified Example 3.
Figure 14B:
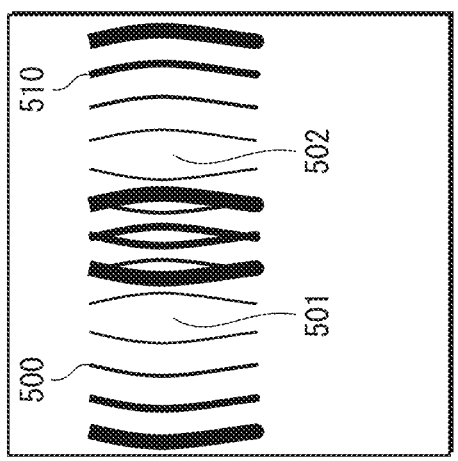

A wavefront image in the case of transmitting a push pulse to one place will be the wavefront image shown in FIG. 14A, whereas a wavefront image in the case of transmitting the push pulse to two places will be the wavefront image shown in FIG. 14B. Here, in FIG. 14A and FIG. 14B, the wavefront of a shear wave that has been generated by the push pulse applied to a position 501 is represented as a wavefront 500. In FIG. 14B, the wavefront of a shear wave that has been generated by the push pulse applied to a position 502 is represented as a wavefront 510.

Figure 14C:
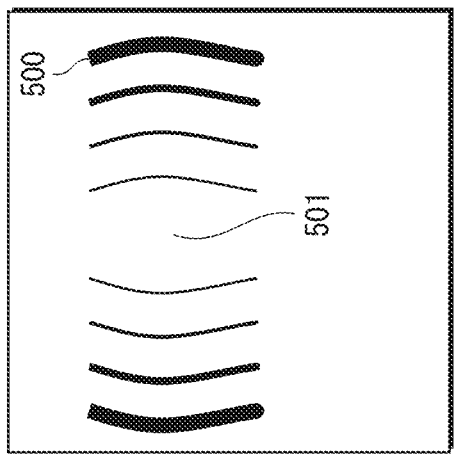

As shown in the wavefront image in FIG. 14C, the mode of displaying wavefronts, with respect to the luminance and the color for example, may be varied according to the push pulse that generated the wavefronts. The following describes the method for associating a wavefront with a push pulse. The operations are similar to those in Modified Example 2, but additionally include a determination as to which push pulse is the cause of the wavefront of a transmitted wave or a reflected wave. Specifically, in step S202, a transmitted wave that was generated in the vicinity of the position to which a first push pulse was applied is determined to be a transmitted wave that was generated by the first push pulse, and a transmitted wave that was generated in the vicinity of the position to which a second push pulse was applied is determined to be a transmitted wave that was generated by the second push pulse. Furthermore, in steps S207 and S208, the wavefront is determined to be the wavefront of a transmitted wave or the wavefront of a reflected wave that was generated by the push pulse that is the same as the push pulse that generated the reference wavefront. These operations realize a determination for every wavefront as to which push pulse is the cause of the wavefront of a transmitted wave or a reflected wave. Note that in the same manner as in Modified Example 2, only wavefronts resulting from one push pulse may be displayed, for example.

Conclusion

In the present modified example, a description has been given of the case of transmitting a push pulse a plurality of times. Such a configuration makes it possible to check the wavefront of the shear wave even in the case where a push pulse is simultaneously applied to a plurality of places. Also, in a region through which both the wavefronts resulting from the first push pulse and the wavefronts resulting from the second push pulse pass, it is possible to check whether or not reflection or the like has occurred, and to avoid the situation where it is difficult to check the propagation state due to interference of transmitted waves with each other. Thus, the present modified example makes it possible to provide the examiner with more accurate information about the propagation state of the shear wave.

Embodiment 2

Figure 15:
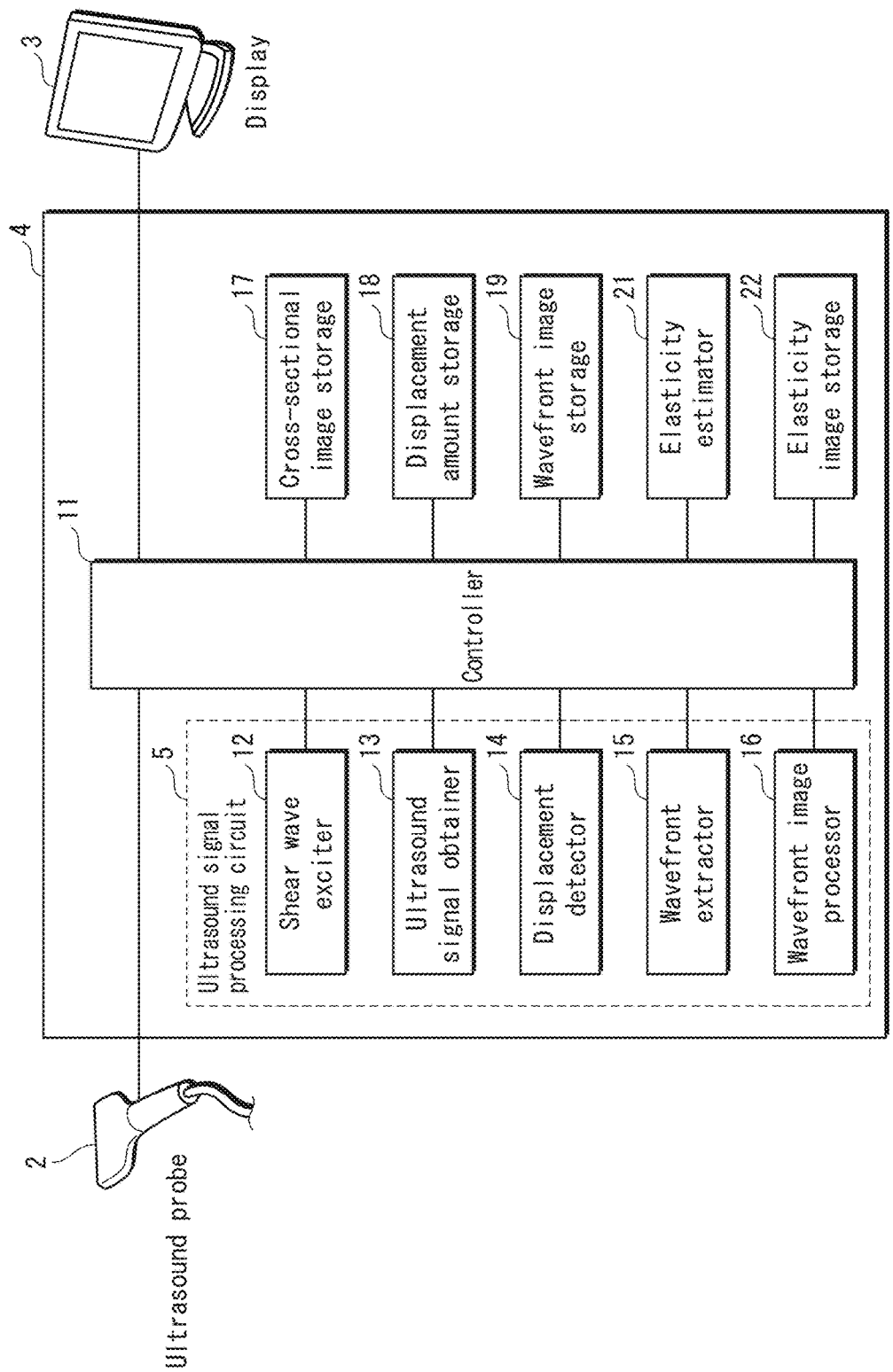
FIG. 15 is a block diagram of an ultrasound diagnostic device 4 according to Embodiment 2.

In Embodiment 1, the case of providing only wavefront images and indicating only the propagation state of the shear wave has been described. In contrast, the present embodiment describes the case of providing cross-sectional images and the hardness of a tissue as well as wavefront images.
Configuration FIG. 15 is a block diagram of an ultrasound diagnostic device 4 according to Embodiment 2. Note that the same reference signs are used for the same components as those in FIG. 1, and the description thereof is omitted.

An elasticity estimator 21 estimates the elastic modulus at each coordinate point in the region of interest based on the wavefront image data stored in the wavefront image storage 19, and outputs the results in the form of an elasticity image, in which the elastic modulus at each coordinate point is shown with a color, to an elasticity image storage 22. Specifically, the elasticity estimator 21 calculates the travelling distance of a wavefront from pieces of wavefront image data that are temporally successive. The travelling distance of a wavefront indicates the speed of the shear wave at the position that the wavefront has passed through. Since an elastic modulus (e.g., Young's modulus) can be calculated from the speed of the shear wave, the elastic modulus at the position that the wavefront has passed through can be calculated.

Figure 16A:
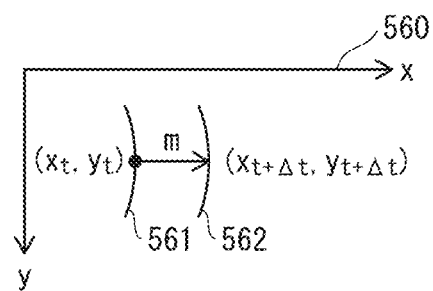
FIG. 16A is a schematic diagram showing an elasticity estimation process according to Embodiment 2.
Figure 16B:
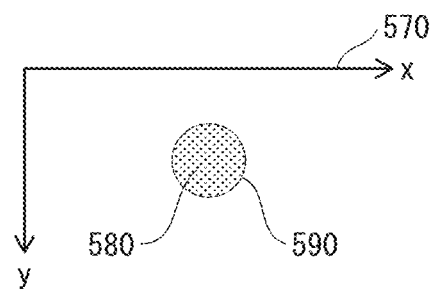
FIG. 16B is an example of an elasticity image according to Embodiment 2.

The elasticity image storage 22 stores the elasticity image. The elasticity image storage 22 is realized with a storage medium such as a RAM, a flash memory, or a hard disk.
Operations FIGS. 16A and 16B are schematic diagrams showing shear wave speed calculation operations. FIG. 16A is a wavefront image 560, which is a single image generated by combining a wavefront image at a given point in time t and a wavefront image at a point in time t+Δt. Here, it is assumed that a wavefront 561 at the point in time t and a wavefront 562 at the point in time t+Δt indicate the same wavefront. The elasticity estimator 21 performs the correlation process between the wavefront 561 and the wavefront 562, thereby detecting a coordinate point $(x_{t+\Delta t}, y_{t+\Delta t})$ on the wavefront 562 that corresponds to a coordinate point $(x_t, y_t)$ on the wavefront 561. Thus, it is possible to estimate that the shear wave that passed through the coordinate point $(x_t, y_t)$ at the point in time t reached the coordinate point $(x_{t+\Delta t}, y_{t+\Delta t})$ at the point in time t+Δt. Therefore, it is possible to estimate the speed $v(x_t, y_t)$ of the shear wave that passed through the coordinates $(x_t, y_t)$ to be a value obtained by dividing a distance m between the coordinate point $(x_t, y_t)$ and the coordinate point $(x_{t+\Delta t}, y_{t+\Delta t})$ by the required period of time Δt. That is, the equation $v(x_t, yt)=m/\Delta t=\sqrt{\{(x_{t+\Delta t}-x_t)^2+(y_{t+\Delta t}-yt)^2\}}/\Delta t$ is obtained.

The elasticity estimator 21 performs the above operation for every wavefront, obtains the speed of the shear wave at every coordinate point that the wavefront passed through, and calculates the elastic modulus based on the speed of the shear wave. The elasticity estimator 21 generates an elasticity image, in which color information is mapped, based on the elastic modulus. For example, as shown in FIG. 16B, the elasticity estimator 21 generates an elasticity image 570 in which coordinate points are color-coded e.g., coordinate points with an elastic modulus greater than or equal to a predetermined value are indicated in red, and coordinate points with an elastic modulus smaller than the predetermined value are indicated in green. Classification is not limited to two-level classification, and classification and color coding may be performed on a scale with a given number of levels. In FIG. 16B, a region 580 is a region having an elastic modulus that is greater than or equal to a predetermined value, and corresponds to an inclusion 590. Note that the inclusion 590 cannot be seen directly on the elasticity image. The elasticity estimator 21 outputs the elasticity image thus generated to the elasticity image storage 22.

Figure 17B:
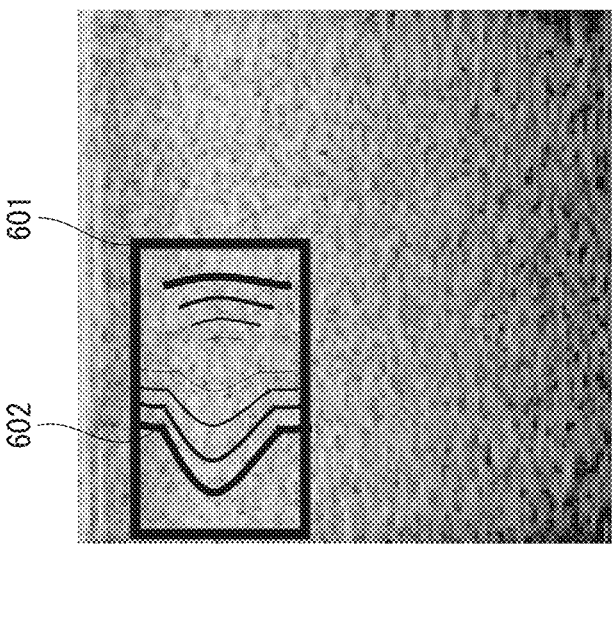
FIGS. 17A and 17B are examples of a mode in which the ultrasound diagnostic device 4 according to Embodiment 2 displays a wavefront image.
Figure 17A:
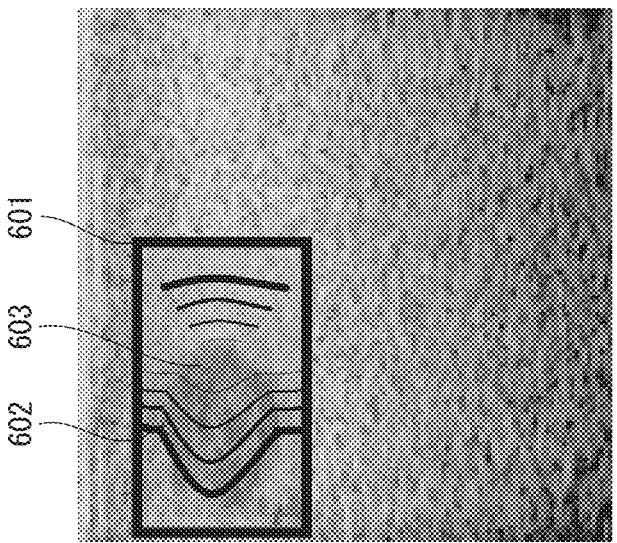

The controller 11 displays, for example, the cross-sectional image signals stored in the cross-sectional image storage 17 with the elasticity image stored in the elasticity image storage 22 and wavefront images superposed thereon. Note that the controller 11 performs geometric conversion on all of: the cross-sectional image signals; the elasticity image; and the wavefront image so as to form image data to be displayed on the screen, and further performs envelope detection and luminance conversion by logarithmic compression on the cross-sectional image signals. FIG. 17A shows an example of a cross-sectional image converted from the cross-sectional image signals, with the elasticity image and the wavefront images superposed thereon. A region 601 is the region of interest, on which the elasticity image and the wavefront images are superposed. A region 603 is a region on the elasticity image and has an elastic modulus that is greater than or equal to a predetermined value. A wavefront 602 is also superposed on the region 601. As described above, the propagation speed of the shear wave is higher for a higher elastic modulus, i.e., higher for a harder tissue. Therefore, as shown in FIG. 17A, the wavefront 602 in the region 603 has a shape that protrudes in the travelling direction. Note that as shown in FIG. 17B for example, the controller 11 may superpose wavefront images on a cross-sectional image converted from the cross-sectional image signals.
Conclusion In the present embodiment, a description has been given of the case of displaying the measurement results of the elastic modulus of a tissue, with an image showing the propagation of the shear wave superposed thereon. Such a configuration makes it possible to more accurately evaluate the reliability of the measurement results of the elastic modulus of the tissue because it is possible to check the propagation of the shear wave at a position concerned.

Other Modified Examples According to Embodiments (1) In each Embodiment and each Modified Example, a description has been given of the case where the displacement detector 14 performs detection of displacements between the cross-sectional image signals before a push pulse is transmitted, which serve as reference cross-sectional image signals, and the cross-sectional image signals after the push pulse is transmitted, using pattern matching, a correlation process, or the like. However, the present invention is not necessarily limited to this case. For example, the obtainment of cross-sectional image signals in step S20 may be omitted, and the cross-sectional image signals that have been obtained by capturing an image of the region of interest and have been stored in advance to the cross-sectional image storage 17, or representative cross-sectional image signals in the region of interest, may be used as the reference cross-sectional image signals. Also, from among sets of cross-sectional image signals after the push pulse is transmitted, one of two sets of cross-sectional image signals at two different points in time with a given time difference therebetween may be used as the reference cross-sectional image signals for the other set.

(2) In each Embodiment and each Modified Example, a description has been given of the case where the ultrasound signal obtainer 13 generates acoustic line signals, the cross-sectional image storage 17 stores the acoustic line signals, and the displacement detector 14 performs displacement detection by using cross-sectional image signals that are one screen's worth of acoustic line signals. However, the present invention is not necessarily limited to this case. For example, the ultrasound signal obtainer 13 may perform envelope detection, luminance conversion by logarithmic compression, and geometric conversion for forming image data to be displayed on the screen, on the cross-sectional image signals, thereby converting the cross-sectional image signals to cross-sectional images, and the cross-sectional image storage 17 may store the cross-sectional images. With this configuration, it is unnecessary for the controller 11 to perform geometric conversion on wavefront images, and it is also unnecessary to perform luminance conversion by logarithmic compression, or geometric conversion on the cross-sectional images stored in the cross-sectional image storage 17, and the cross-sectional images as they are can be displayed on the display 3.

(3) In each Embodiment and Modified Examples 2 and 3, a description has been given of the case where the displacement region extractor 31 extracts the displacement region from the entire region of a displacement image. However, the present invention is not necessarily limited to this case. For example, with respect to the displacement image immediately after a push pulse was applied, the displacement region extractor 31 may extract the displacement region only from the vicinity of the position to which the push pulse was applied. This configuration can reduce the amount of calculation, and makes it possible to avoid erroneously detecting noise as wavefronts, by excluding regions in which the shear wave obviously does not exist, from the target of extraction. Note that the way of limiting the range of extraction of the displacement region is not limited to the case above. For example, in the case where no shear wave is detected with respect to a given value of the y coordinate, the given value of y coordinate may be excluded from the target of extraction of the displacement region at subsequent points in time.

Similarly, the temporal filter 34 may perform the temporal filtering process based on the point in time at which a push pulse was applied. For example, with respect to the wavefront image immediately after the push pulse was applied, the temporal filter 34 may exclude wavefronts that are not in the vicinity of the position to which the push pulse was applied, regarding them as noise. This configuration makes it possible to avoid erroneously detecting noise that exists in regions in which the shear wave obviously cannot exist, as wavefronts.

(4) In each Embodiment and each Modified Example, a description has been given of the case where the spatial filter 33 and the temporal filter 34 individually perform a filtering process. However, the present invention is not necessarily limited to this case. For example, the spatial filtering process and the temporal filtering process may be simultaneously performed.

(5) In each Embodiment and Modified Examples 2 and 3, a description has been given of the case where the displacement region extractor 31 extracts a region in which the displacement amount $\delta$ is large by using a dynamic threshold, where, for each value of the y coordinate, the displacement amount $\delta$ is considered as a function of the x coordinate, and for each value of the x coordinate, the displacement amount $\delta$ is considered as a function of the y coordinate. However, the present invention is not necessarily limited to this case. For example, the displacement region extractor 31 may perform the process of extracting a region in which the displacement amount $\delta$ is large with respect to only all the values of the y coordinate, where, for each value of the y coordinate, the displacement amount $\delta$ is considered as a function of the x coordinate, or conversely, perform the process of extracting a region in which the displacement amount $\delta$ is large with respect to only all the values of the x coordinate, where, for each value of the x coordinate, the displacement amount $\delta$ is considered as a function of the y coordinate. Alternatively, the displacement region extractor 31 may extract a region in which the displacement amount $\delta$ is large in two dimensions, where the displacement amount $\delta$ is considered as a function of the x and y coordinates.

(6) In each Embodiment and Modified Examples 2 and 3, a description has been given of the case where the thinner 32 performs the thinning process on the displacement region. However, the present invention is not necessarily limited to this case. For example, the displacement region extractor 31 may connect pixels with a large displacement in the displacement region with a line, and regard such lines as wavefronts. This configuration makes the thinning process unnecessary.

(7) In Modified Example 1, a description has been given of the case where the displacement peak detector 36 detects the point in time at which the displacement amount peaks from the displacement images by performing the correlation process. However, the present invention is not necessarily limited to this case. For example, a threshold may be provided for correlation values obtained by the correlation process, and the displacement peak detector 36 may detect a period of time in which a correlation value that is greater than the threshold is detected. This configuration makes it possible to detect not only the exact point in time at which the display amount peaks, but also nearby points in time thereof, and to more accurately detect wavefronts. Conversely, a lower limit threshold may be provided for correlation values obtained by the correlation process, and in the case where a correlation value that is smaller than the threshold is detected, the displacement peak detector 36 may not detect the correlation value as a peak. This configuration makes it possible to avoid erroneously detecting a wobble occurred at a point in time when there was no passing wavefront, for example, as a wavefront.

(8) In each Embodiment and each Modified Example, a description has been given of the case where the wavefront image processor 16 modifies the mode of displaying wavefronts. However, the present invention is not necessarily limited to this case. For example, the wavefront image processor 16 may not change the mode of displaying the wavefront image data stored in the wavefront image storage 19.

(9) In each Embodiment and each Modified Example, a description has been given of the case where, in step S20, the ultrasound signal obtainer 13 performs transmission beamforming such that transmission ultrasound waves reach the transmission focal point at the same time, performs a delay-and-sum process on element reception signals for each transmission event, and generates acoustic line signals. However, the present invention is not necessarily limited to this case. For example, the ultrasound signal obtainer 13 may transmit a transmission ultrasound wave having a planer wave shape by simultaneously emitting ultrasound waves from the transducers that constitute the ultrasound probe 2. In this case, it is unnecessary to limit the reception focal point to be in the vicinity of the transmission focal point or to be on the same line as the transmission focal point, and therefore, when obtaining acoustic line signals that constitute one cross-sectional image, it is possible to obtain one image's worth of acoustic line signals at a time, instead of obtaining one acoustic line signal at each transmission event. Consequently, it is possible to improve the frame rate of cross-sectional image signals.

(10) In each Embodiment and each Modified Example, a description has been given of the case where the ultrasound diagnostic device is configured to be connected to the display 3. However, the present invention is not necessarily limited to this case. For example, the display 3 may be built into the ultrasound diagnostic device 1. Alternatively, the ultrasound diagnostic device 1 may not be connected to the display 3, and the wavefront image data generated by the wavefront image processor 16 may be stored to a storage medium, or output to another device via a network.

Similarly, the ultrasound probe 2 may be built into the ultrasound diagnostic device. Alternatively, the ultrasound probe 2 may have the ultrasound signal obtainer 13, and the ultrasound diagnostic device without the ultrasound signal obtainer 13 may obtain acoustic line signals from the ultrasound probe 2. Alternatively, the ultrasound diagnostic device may read acoustic line data or cross-sectional images from a recording medium, or obtain acoustic line data or cross-sectional images from another device via a network. Similarly, the ultrasound diagnostic device may obtain cross-sectional images or an elasticity image, on which wavefront images are to be superposed, from a recording medium or another device via a network.

(11) In each Embodiment and each Modified Example, a description has been given of the case where the controller 11 displays the wavefronts in the form of a moving image. However, the present invention is not necessarily limited to this case. For example, the controller 11 may perform geometrical conversion on some of the pieces of wavefront image data so that they serve as pieces of image data to be displayed on the screen, and display the pieces of wavefront image data that have undergone geometric conversion on the display 3. Alternatively, for example, the controller 11 may perform geometrical conversion on one of the pieces of wavefront image data so that it serves as a piece of image data to be displayed on the screen, and display the piece of wavefront image data that has undergone geometric conversion on the display 3. Alternatively, for example, the controller 11 may first superpose and combine the pieces of wavefront image data with each other to form one piece of image data, next perform geometrical conversion on the piece of image data so that it serves as a piece of image data to be displayed on the screen, and then display the piece of image data that has undergone geometric conversion on the display 3.

(12) The ultrasound diagnostic device pertaining to each Embodiment and each Modified Example may be entirely or partially implemented as a single chip or multiple chip integrated circuit, implemented as a computer program, or implemented in any other form. For example, the wavefront extractor may be implemented as one chip, the displacement region extractor may be implemented as one chip, and the thinner, etc., implemented as another chip.

When implemented as an integrated circuit, typically this be as a large scale integration (LSI). LSI is referred to here, but according to the degree of integration this may be referred to as IC, system LSI, super LSI, or ultra LSI.

Further, methods of circuit integration are not limited to LSI and function blocks may be implemented by dedicated circuits or general-purpose processors. After LSI manufacture, a field programmable gate array (FPGA) or reprogrammable processor that can set and reconfigure circuit cells and connections within the LSI may be used.

Further, should circuit integration technology replacing LSI appear as a result of progress in semiconductor technology or another technology derivative technology, integration of functional blocks may of course be achieved by using such technology.

Further, the ultrasound diagnostic device pertaining to each Embodiment and each Modified Example may be implemented as a program written to a storage medium and a computer that executes the program. The storage medium may be any kind of storage medium, such as a memory card, CD-ROM, etc. Further, the ultrasound diagnostic device pertaining to the present invention may be implemented as a program downloaded via a network and a computer that downloads the program via the network and executes the program.

(13) The Embodiments described above illustrate specific preferred examples of the present invention. The numerical values, shapes, materials, elements, positions and connections of the elements, steps, order of steps, etc., are examples and not intended to limit the invention. Further, among elements of the embodiments, processes that are not recited in independent claims that indicate the most significant concepts of the invention are described as optional elements of further preferential aspects of the invention.

Further, in order to aid understanding of the invention, the scale of elements in each drawing for the Embodiments above may differ from actual scale. Further, the present invention is not limited to the description of the Embodiments above, and may be appropriately modified without departing from the scope of the present invention.

Furthermore, although circuit components, lead lines, etc., exist on the substrate in the ultrasound diagnostic apparatus, electrical wiring and electrical circuits can be implemented in various ways based on ordinary skill in the art, and are not directly related to description of the present invention, and therefore description thereof is omitted. Note that the drawings indicated above are schematic, and not necessarily exact representations.

Supplementary Explanation (1) The ultrasound diagnostic device pertaining to an Embodiment is an ultrasound diagnostic device that transmits a push pulse, which is ultrasound that converges on a particular part inside a subject to apply physical pressure to tissue at the particular part, by using an ultrasound probe, and detects a process in which the tissue at the particular part acts as a vibration source due to the pressure and a shear wave propagates to adjacent tissue, by repeating transmission of ultrasound to the subject and reception of reflected ultrasound from the subject subsequent to transmission of the push pulse, the ultrasound diagnostic device comprising an ultrasound signal processing circuit, wherein the ultrasound signal processing circuit includes: a displacement detector that obtains a plurality of reception signals in a time series by performing transmission of ultrasound to the subject and reception of reflected ultrasound from the subject, subsequent to transmission of the push pulse, and detects a displacement amount of the tissue inside the subject at each of a plurality of points in time at which the plurality of reception signals are respectively obtained; a wavefront extractor that extracts, based on the displacement amount of the tissue at each of the plurality of points in time at which the plurality of reception signals are respectively obtained, a wavefront of the shear wave at the corresponding point in time; and a wavefront image processor that generates a wavefront image that indicates a wavefront of the shear wave at each of the plurality of points in time at which the plurality of reception signals are respectively obtained.

Further, the method for controlling an ultrasound diagnostic device pertaining to an Embodiment is a method for controlling an ultrasound diagnostic device that transmits a push pulse, which is ultrasound that converges on a particular part inside a subject to apply physical pressure to tissue at the particular part, by using an ultrasound probe, and detects a process in which the tissue at the particular part acts as a vibration source due to the pressure and a shear wave propagating to adjacent tissue, by repeating transmission of ultrasound to the subject and reception of reflected ultrasound from the subject subsequent to transmission of the push pulse, the method comprising: obtaining a plurality of reception signals in a time series by performing transmission of ultrasound to the subject and reception of reflected ultrasound from the subject, subsequent to transmission of the push pulse, and detecting a displacement amount of the tissue inside the subject at each of a plurality of points in time at which the plurality of reception signals are respectively obtained; extracting, based on the displacement amount of the tissue at each of the plurality of points in time at which the plurality of reception signals are respectively obtained, a wavefront of the shear wave at the corresponding point in time; and generating a wavefront image that indicates a wavefront of the shear wave at each of the plurality of points in time at which the plurality of reception signals are respectively obtained.

According to the present disclosure, the examiner can check an image of the wavefronts at each point in time in the period during which the shear wave propagates, and therefore the examiner can check whether or not the wavefronts of the shear wave have propagated without being reflected or deflected. Furthermore, in the case where reflection or deflection of the shear wave occurred, the examiner can easily estimate the position where such a situation occurred, based on the shapes of the wavefronts, the positions of the wavefronts at each point in time, the propagation speeds of the wavefronts indicated by the positions, and the orientations of the wavefronts. Therefore, in the case where the examiner has been unable to obtain the hardness of the tissue inside the subject due to deflection or reflection of the shear wave, the examiner can perform re-examination after taking appropriate measures, such as changing the position of the ultrasound probe, changing the posture of the examinee, and changing the position to which a push pulse is applied, based on how the shear wave has propagated.

(2) Further, the ultrasound diagnostic device according to (1), above, pertaining to an embodiment, may be configured so that the wavefront image processor further generates an image indicating temporal changes of the wavefront.

This configuration allows the examiner to check the positions and the propagation directions of the wavefronts in a time series, and to more accurately check the propagation of the shear wave.

(3) Further, the ultrasound diagnostic device according to (2), above, pertaining to an embodiment, may be configured so that the image indicating the temporal changes of the wavefront is a moving image.

This configuration allows the examiner to check the propagation of the shear wave in a more intuitive manner.

(4) Further, the ultrasound diagnostic device according to (1) or (2), above, pertaining to an embodiment, may be configured so that the wavefront image processor outputs the wavefront image after superposing the wavefront image on an elasticity image that indicates an elasticity of each of regions of the tissue inside the subject.

This configuration allows the examiner to check both the elasticity image and the propagation of the wavefronts at the same time, and to obtain specific information about the reliability of each region in the elasticity image.

(5) Further, the ultrasound diagnostic device according to (1) or (2), above, pertaining to an embodiment, may be configured so that the wavefront image processor outputs the wavefront image after superposing the wavefront image on a cross-sectional image that corresponds to the tissue inside the subject.

This configuration allows the examiner to check both the cross-sectional image and the propagation of the wavefronts at the same time, and to more accurately estimate the state of the tissue inside the subject, taking both the cross-sectional image and the propagation of the shear wave into consideration.

(6) Further, the ultrasound diagnostic device according to any one of (1) to (5), above, pertaining to an embodiment, may be configured so that the wavefront extractor extracts, with respect to each of the plurality of reception signals, a displacement region in which a displacement amount is greater than a threshold, and extracts a wavefront of the shear wave at a point in time at which the corresponding reception signal is obtained, by performing a thinning process on the corresponding displacement region thus extracted.

This configuration makes it possible to extract a wavefront based on the magnitude of a displacement.

(7) Further, the ultrasound diagnostic device according to any one of (1) to (5), above, pertaining to an embodiment, may be configured so that the wavefront extractor detects a point in time at which a displacement indicated by the plurality of reception signals takes an extremum thereof with respect to each of positions inside the subject by performing a correlation process, and by extracting a displacement region with respect to each of the plurality of reception signals based on the point in time at which the displacement takes the extremum, extracts a wavefront of the shear wave at a point in time at which the corresponding reception signal is obtained.

This configuration makes it possible to detect each wavefront based on temporal changes in displacements, regardless of the number of times the wavefront passes through, or the travelling direction of the wavefront.

(8) Further, the ultrasound diagnostic device according to any one of (1) to (7), above, pertaining to an embodiment, may be configured so that the wavefront image processor modifies a mode in which each of wavefronts extracted by the wavefront extractor is displayed, such that wavefronts at different points in time that correspond to the plurality of reception signals are displayed in different modes.

This configuration makes it easy to distinguish between wavefronts, and makes it possible to more accurately check the propagation of the shear wave.

(9) Further, the ultrasound diagnostic device according to (8), above, pertaining to an embodiment, may be configured so that the wavefront image processor makes a difference between modes in which a plurality of wavefronts at different points in time are displayed, by varying respective lines of the plurality of wavefronts from each other, at least in thickness, color, luminance, or type.

(10) Further, the ultrasound diagnostic device according to (8), above, pertaining to an embodiment, may be configured so that the wavefront image processor expresses each wavefront as an arrow having an orientation and a length that respectively indicate a propagation direction and a propagation speed of the shear wave, and makes a difference between modes in which a plurality of wavefronts at different points in time are displayed, by varying respective arrows of the plurality of wavefronts from each other, at least in thickness, color, or luminance.

The configurations shown in (9) and (10) above make it possible to more clearly distinguish between wavefronts at different points in time, and to more accurately check the propagation of the shear wave.

(11) Further, the ultrasound diagnostic device according to (8), above, pertaining to an embodiment, may be configured so that the wavefront image processor displays, from among wavefronts extracted by the wavefront extractor, only wavefronts related to shear waves that have a same travelling direction.

(12) Further, the ultrasound diagnostic device according to any one of (1) to (10), above, pertaining to an embodiment, may be configured so that the wavefront image processor varies a mode in which a wavefront is displayed, for each travelling direction of the shear wave.

The configurations shown in (11) and (12) above make it possible to easily check whether or not reflection of the shear wave has occurred, and to check either a set of transmitted waves or a set of reflected waves alone even when they interfere with each other.

(13) Further, the ultrasound diagnostic device according to any one of (1) to (12), above, pertaining to an embodiment, may be configured so that the wavefront extractor extracts an interface at which a travelling direction of the shear wave changes, and the wavefront image processor superposes the interface on the wavefront.

This configuration makes it possible to easily check the location of the cause of reflection of the shear wave.

(14) Further, the ultrasound diagnostic device according to any one of (1) to (13), above, pertaining to an embodiment, may be configured so that when the push pulse is defined as a first push pulse, the ultrasound diagnostic device causes the ultrasound probe to further transmit a second push pulse, and the wavefront image processor makes a difference between a mode in which wavefronts of a shear wave generated by the first push pulse are displayed and a mode in which wavefronts of a shear wave generated by the second push pulse are displayed.

This configuration makes it possible to, when a push pulse is transmitted twice or more and shear waves interfere with each other, easily check the propagation of each shear wave.

(15) Further, the ultrasound diagnostic device according to any one of (1) to (14), above, pertaining to an embodiment, may further comprise an elasticity estimation unit that assumes that a travelling distance between same waveforms at different points in time indicates a propagation speed of the shear wave during a period between the different points in time, thereby estimating an elasticity of each of regions through which the shear wave passed through from among regions of the tissue inside the subject.

This configuration makes it possible to simultaneously perform detection of wavefronts and measurement of the elasticity of a tissue, and also makes it possible to easily check the reliability of the elasticity of the tissue from the propagation state of the shear wave, and to check the cause of the low reliability of the elasticity of the tissue.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound diagnostic device that transmits a push pulse, which is ultrasound that converges on a particular part inside a subject to apply physical pressure to tissue at the particular part, by using an ultrasound probe, and detects a process in which the tissue at the particular part acts as a vibration source due to the pressure and a shear wave propagates to adjacent tissue, by repeating transmission of ultrasound to the subject and reception of reflected ultrasound from the subject subsequent to transmission of the push pulse,
    the ultrasound diagnostic device comprising an ultrasound signal processing circuit, wherein
    the ultrasound signal processing circuit includes:
    a displacement detector that obtains a plurality of reception signals in a time series by performing transmission of ultrasound to the subject and reception of reflected ultrasound from the subject, subsequent to transmission of the push pulse, and detects a displacement amount of the tissue inside the subject at each of a plurality of points in time at which the plurality of reception signals are respectively obtained;
    a wavefront extractor that extracts, based on the displacement amount of the tissue at each of the plurality of points in time at which the plurality of reception signals are respectively obtained, a wavefront of the shear wave at the corresponding point in time; and
    a wavefront image processor that generates a wavefront image that indicates a wavefront of the shear wave at each of the plurality of points in time at which the plurality of reception signals are respectively obtained.

2. The ultrasound diagnostic device according to claim 1, wherein
    the wavefront image processor further generates an image indicating temporal changes of the wavefront.

3. The ultrasound diagnostic device according to claim 2, wherein
    the image indicating the temporal changes of the wavefront is a moving image.

4. The ultrasound diagnostic device according to claim 1, wherein
    the wavefront image processor outputs the wavefront image after superposing the wavefront image on an elasticity image that indicates an elasticity of each of regions of the tissue inside the subject.

5. The ultrasound diagnostic device according to claim 1, wherein
    the wavefront image processor outputs the wavefront image after superposing the wavefront image on a cross-sectional image that corresponds to the tissue inside the subject.

6. The ultrasound diagnostic device according to claim 1, wherein
    the wavefront extractor extracts, with respect to each of the plurality of reception signals, a displacement region in which a displacement amount is greater than a threshold, and extracts a wavefront of the shear wave at a point in time at which the corresponding reception signal is obtained, by performing a thinning process on the corresponding displacement region thus extracted.

7. The ultrasound diagnostic device according to claim 1, wherein
the wavefront extractor detects a point in time at which a displacement indicated by the plurality of reception signals takes an extremum thereof with respect to each of positions inside the subject by performing a correlation process, and by extracting a displacement region with respect to each of the plurality of reception signals based on the point in time at which the displacement takes the extremum, extracts a wavefront of the shear wave at a point in time at which the corresponding reception signal is obtained.

8. The ultrasound diagnostic device according to claim 1, wherein
the wavefront image processor modifies a mode in which each of wavefronts extracted by the wavefront extractor is displayed, such that wavefronts at different points in time that correspond to the plurality of reception signals are displayed in different modes.

9. The ultrasound diagnostic device according to claim 8, wherein
the wavefront image processor makes a difference between modes in which a plurality of wavefronts at different points in time are displayed, by varying respective lines of the plurality of wavefronts from each other, at least in thickness, color, luminance, or type.

10. The ultrasound diagnostic device according to claim 8, wherein
the wavefront image processor expresses each wavefront as an arrow having an orientation and a length that respectively indicate a propagation direction and a propagation speed of the shear wave, and makes a difference between modes in which a plurality of wavefronts at different points in time are displayed, by varying respective arrows of the plurality of wavefronts from each other, at least in thickness, color, or luminance.

11. The ultrasound diagnostic device according to claim 1, wherein
the wavefront image processor displays, from among wavefronts extracted by the wavefront extractor, only wavefronts related to shear waves that have a same travelling direction.

12. The ultrasound diagnostic device according to claim 1, wherein
the wavefront image processor varies a mode in which a wavefront is displayed, for each travelling direction of the shear wave.

13. The ultrasound diagnostic device according to claim 1, wherein
the wavefront extractor extracts an interface at which a travelling direction of the shear wave changes, and
the wavefront image processor superposes the interface on the wavefront.

14. The ultrasound diagnostic device according to claim 1, wherein
when the push pulse is defined as a first push pulse, the ultrasound diagnostic device causes the ultrasound probe to further transmit a second push pulse, and
the wavefront image processor makes a difference between a mode in which wavefronts of a shear wave generated by the first push pulse are displayed and a mode in which wavefronts of a shear wave generated by the second push pulse are displayed.

15. The ultrasound diagnostic device according to claim 1, further comprising an elasticity estimation unit that assumes that a travelling distance between same waveforms at different points in time indicates a propagation speed of the shear wave during a period between the different points in time, thereby estimating an elasticity of each of regions through which the shear wave passed through from among regions of the tissue inside the subject.

16. A method for controlling an ultrasound diagnostic device that transmits a push pulse, which is ultrasound that converges on a particular part inside a subject to apply physical pressure to tissue at the particular part, by using an ultrasound probe, and detects a process in which the tissue at the particular part acts as a vibration source due to the pressure and a shear wave propagates to adjacent tissue, by repeating transmission of ultrasound to the subject and reception of reflected ultrasound from the subject subsequent to transmission of the push pulse, the method comprising:
obtaining a plurality of reception signals in a time series by performing transmission of ultrasound to the subject and reception of reflected ultrasound from the subject, subsequent to transmission of the push pulse, and detecting a displacement amount of the tissue inside the subject at each of a plurality of points in time at which the plurality of reception signals are respectively obtained;
extracting, based on the displacement amount of the tissue at each of the plurality of points in time at which the plurality of reception signals are respectively obtained, a wavefront of the shear wave at the corresponding point in time; and
generating a wavefront image that indicates a wavefront of the shear wave at each of the plurality of points in time at which the plurality of reception signals are respectively obtained.

* * * * *